(12) United States Patent
Ibrahim et al.

(10) Patent No.: US 9,259,467 B2
(45) Date of Patent: Feb. 16, 2016

(54) MAMMALIAN RECEPTORS AS TARGETS FOR ANTIBODY AND ACTIVE VACCINATION THERAPY AGAINST MOLD INFECTIONS

(71) Applicant: Los Angeles Biomedical Research Institute at Harbor-UCLA Medical Center, Torrance, CA (US)

(72) Inventors: Ashraf S. Ibrahim, Irvine, CA (US); Mingfu Liu, Carson, CA (US); Brad Spellberg, Rancho Palos Verdes, CA (US); Scott Filler, Rancho Palos Verdes, CA (US); Yue Fu, Torrance, CA (US); John E. Edwards, Palos Verdes Estates, CA (US)

(73) Assignee: LOS ANGELES BIOMEDICAL RESEARCH INSTITUTE AT HARBOR-UCLA MEDICAL CENTER, Torrance, CA (US)

(*) Notice: Subject to any disclaimer, the term of this patent is extended or adjusted under 35 U.S.C. 154(b) by 0 days.

(21) Appl. No.: 14/139,683

(22) Filed: Dec. 23, 2013

(65) Prior Publication Data
US 2014/0112941 A1    Apr. 24, 2014

Related U.S. Application Data

(63) Continuation of application No. 12/874,126, filed on Sep. 1, 2010, now abandoned.

(60) Provisional application No. 61/239,026, filed on Sep. 1, 2009.

(51) Int. Cl.
| A61K 39/395 | (2006.01) |
| A61K 39/00 | (2006.01) |
| A61K 31/713 | (2006.01) |
| C07K 16/14 | (2006.01) |
| C12N 15/113 | (2010.01) |

(52) U.S. Cl.
CPC ......... *A61K 39/39575* (2013.01); *A61K 31/713* (2013.01); *A61K 39/0002* (2013.01); *A61K 39/0005* (2013.01); *C07K 16/14* (2013.01); *C12N 15/1138* (2013.01); *A61K 2039/505* (2013.01); *C07K 2317/76* (2013.01); *C07K 2317/77* (2013.01); *C12N 2310/14* (2013.01); *C12N 2310/531* (2013.01); *C12N 2799/027* (2013.01); *C12N 2799/06* (2013.01)

(58) Field of Classification Search
None
See application file for complete search history.

(56) References Cited

U.S. PATENT DOCUMENTS

| 4,235,877 A | 11/1980 | Fullerton et al. |
| 4,372,945 A | 2/1983 | Likhite |
| 4,474,757 A | 10/1984 | Arnon et al. |
| 5,013,556 A | 5/1991 | Woodle et al. |
| 5,108,921 A | 4/1992 | Low et al. |
| 5,166,320 A | 11/1992 | Wu et al. |
| 5,213,804 A | 5/1993 | Martin et al. |
| 5,223,409 A | 6/1993 | Ladner et al. |
| 5,279,833 A | 1/1994 | Rose et al. |
| 5,283,185 A | 2/1994 | Epand et al. |
| 5,334,761 A | 8/1994 | Gebeyehu et al. |
| 5,403,484 A | 4/1995 | Ladner et al. |
| 5,427,908 A | 6/1995 | Dower et al. |
| 5,428,130 A | 6/1995 | Capon et al. |
| 5,516,637 A | 5/1996 | Huang et al. |
| 5,521,291 A | 5/1996 | Curiel et al. |
| 5,542,935 A | 8/1996 | Unger et al. |
| 5,554,386 A | 9/1996 | Groman et al. |
| 5,571,698 A | 11/1996 | Ladner et al. |
| 5,578,475 A | 11/1996 | Jessee et al. |
| 5,580,717 A | 12/1996 | Dower et al. |
| 5,580,859 A | 12/1996 | Felgner et al. |
| 5,589,466 A | 12/1996 | Felgner et al. |
| 5,650,150 A | 7/1997 | Gillies et al. |
| 5,658,727 A | 8/1997 | Barbas et al. |
| 5,693,762 A | 12/1997 | Queen et al. |
| 5,698,426 A | 12/1997 | Huse et al. |
| 5,733,743 A | 3/1998 | Johnson et al. |
| 5,750,753 A | 5/1998 | Kimae et al. |
| 5,780,225 A | 7/1998 | Wigler et al. |
| 5,807,706 A | 9/1998 | Carter et al. |
| 5,821,047 A | 10/1998 | Garrard et al. |
| 5,877,397 A | 3/1999 | Longerg et al. |
| 5,965,722 A | 10/1999 | Ecker et al. |
| 5,969,108 A | 10/1999 | McCafferty et al. |
| 6,075,181 A | 6/2000 | Kucherlapati et al. |
| 6,096,311 A | 8/2000 | Fanger et al. |
| 6,111,166 A | 8/2000 | Van De Winkel et al. |
| 6,114,598 A | 9/2000 | Kucherlapati et al. |

(Continued)

FOREIGN PATENT DOCUMENTS

WO    WO 9926068    5/1999

OTHER PUBLICATIONS

Gomes et al. Clin. Microbiol. Rev. 24 (2): 411-445, Apr. 2011.*
Webster's II New Riverside University Dictionary, The Riverside Publishing Company, p. 933, 1984.*
Illustrated Stedman's Medical Dictionary, 24th Edition, Williams & Wilkins, Baltimore, p. 707, 1982.*
Liu et al. J. Clin. Invest. 120: 1914-1924, 2010.*
Artis et al., "A Mechanism of Susceptibility to the Mucormycosis in Diabetic Ketoacidosistes Transferrin and Iron Availability ," Diabetes, 31(12):1109-1114 (1982).
Bearer et al., "Cutaneous Zygomycosis Caused by Saksenaea vasiformis in a Diabetic Patient ," Journal of Clinical Microbiology, 32:1823-1824 (1994).

(Continued)

*Primary Examiner* — S. Devi
(74) *Attorney, Agent, or Firm* — Pillsbury Winthrop Shaw Pittman LLP

(57) ABSTRACT

The present invention provides therapeutic compositions and methods for treating and preventing fungal disease or conditions including mucormycosis. The therapeutic methods and compositions of the invention include antibody, antibody fragment, siRNA and vaccine compositions having or directed against a GRP78 polypeptide or an antigenic fragment of the polypeptide.

9 Claims, 11 Drawing Sheets

(56) References Cited

U.S. PATENT DOCUMENTS

| | | | |
|---|---|---|---|
| 6,150,584 | A | 11/2000 | Kucherlapati et al. |
| 6,162,963 | A | 12/2000 | Kucherlapati et al. |
| 6,339,066 | B1 | 1/2002 | Bennett et al. |
| 6,358,931 | B1 | 3/2002 | Cook et al. |
| 6,359,124 | B1 | 3/2002 | Ecker et al. |
| 8,192,740 | B2 | 6/2012 | Kimura |
| 2010/0015128 | A1 | 1/2010 | Lee et al. |

OTHER PUBLICATIONS

Boelaertet et al., "Mucormycosis during Deferoxamine Therapy Is a Siderophore-mediated Infection ," J. Clin. Invest., 91(5):1979-1986 (1993).

Cohen-Adobo et al., "Cunninghamella Infections: Review and Report of Two Cases of Cunninghamella Pneumonia in Immunocompromised Children ," Clinical Infectious Diseases, 17:173-177 (1993).

Davidson et al., "Kringle 5 of Human Plasminogen Induces Apoptosis of Endothelial and Tumor Cells through Surface-Expressed Glucose-Regulated Protein 78," Cancer Res., 65(11):4663-4672 (2005).

Edwards, J., Zygomycosis, pp. 1192-1199 (1989).

Faye et al., Blood Cells Mol Dis., 39(3):229-237 (2007).

Fu et al., "Cloning and functional characterization of the Rhizopus oryzae high affinity iron permease (rFTR1) gene ," FEMS Microbiol. Lett., 235:169-176 (2004).

Gleissner et al., "Improved Outcome of Zygomycosis in Patients with Hematological Diseases? ," Leuk. Lymphoma, 45(7):1351-1360 (2004).

Gomes et al., "Mucormycosis Caused by Unusual Mucormycetes, Non-Rhizopus,-Mucor, and—Lichtheimia Species," Clin. Microbiol. Rev., 24(2):411-445 (2011).

Hardy et al., "Therapeutic angiogenesis of mouse hind limb ischemia by novel peptide activating GRP78 receptor on endothelial cells ," Biochem Pharmacol., 75(4):891-899 (2008).

Husain et al., "Opportunistic Mycelial Fungal Infections in Organ Transplant Recipients: Emerging Importance of Non-Aspergillus Mycelial Fungi ,"Clin. Infect. Dis., 37:221-229 (2003).

Ibrahim et al., "Zygomycosis," Clinical Mycology, 241-251 (2003).

Ibrahim et al., "Liposomal Amphotericin B, and Not Amphotericin B Deoxycholate, Improves Survival of Diabetic Mice Infected with Rhizopus oryzae ," Antimicrob. Agents Chemother., 47:3343-3344 (2003).

Ibrahim et al., "Adherence to and Damage of Endothelial Cells by Cryptococcus neoformans In Vitro: Role of the Capsule ," Infect. Immun., 63(11):4368-4374 (1995).

Ibrahim et al., "Rhizopus oryzae Adheres to, Is Phagocytosed by, and Damages Endothelial Cells In Vitro ," Infect. Immun , 73(2):778-783 (2005).

Ibrahim et al., "Vaccination with Recombinant N-Terminal Domain of Als1p Improves Survival during Murine Disseminated Candidiasis by Enhancing Cell-Mediated, Not Humoral, Immunity ," Infect. Immun., 73:999-1005 (2005).

Ibrahim et al., "The iron chelator deferasirox protects mice from mucormycosis through iron starvation ," J. Clin. Invest., 117:2649-2657 (2007).

Ibrahim et al., "Bacterial Endosymbiosis Is Widely Present among Zygomycetes but Does Not Contribute to the Pathogenesis of Mucormycosis ," J. Infect. Dis., 198(7):1083-1090 (2008).

Illustrated Stedman's Medical Dictionary. 24th Edition, Williams & Wilkins, Baltimore, p. 707 (1982).

Isberg et al., "Multiple P1 Chain Integrins Are Receptors for Invasin, a Protein That Promotes Bacterial Penetration into Mammalian Cells ," 60(5):861-871 (1990).

Jaffe et al., "Culture of Human Endothelial Cells Derived from Umbilical Veins ," J. Clin. Invest., 52(11)2745-2756 (1973).

Jindadamrongwech et al., "Identification of GRP 78 (BiP) as a liver cell expressed receptor element for dengue virus serotype 2," Arch Virol, 149(5):915-927 (2004).

Kamalam et al., "Cutaneous Infection by S Yncephalastrum ," Sabouraudia, 18:19-20 (1980).

Kammoun et al., "GRP78 expression inhibits insulin and ER stress-induced SREBP-1c activation and reduces hepatic steatosis in mice ," J Clin Invest., 119(5):1201-1215 (2009).

Kar et al., "Release of iron from haemoglobin—Apossible source of free radicals in *Diabetes mellitus*," Indian J Exp Biol., 37(2):190-192 (1999).

Kemna et al., "Cokeromyces recurvatus, a Mucoraceous Zygomycete Rarely Isolated in Clinical Laboratories ," Journal of Clinical Microbiology, 32:843-845 (1994).

Kontoyianis et al., "Infections Due to Cunninghamella bertholletiae in Patients with Cancer: Report of Three Cases and Review ," Clinical Infectious Diseases, 18:925-928 (1994).

Kontoyiannis DP., "Decrease in the Number of Reported Cases of Zygomycosis among Patients with *Diabetes mellitus*: A Hypothesis," Clin. Infect. Dis., 44(8):1089-1090 (2007).

Kontoyiannis et al., "Zygomycosis in the 1990s in a Tertiary-Care Cancer Center ," Clin. Infect. Dis., 30(6):851-856 (2000).

Kwon-Chung et al., "Mucormycosis," Medical Mycology, 524-559 (1992).

Kwon-Chung et al., "Pulmonary.Mucormycosis Caused by Cunninghamella elegans in a Patient with Chronic Myelogenous Leukemia ," American Journal of Clinical Pathology, 64:544-548 (1975).

Lee, "GRP78 Induction in Cancer: Therapeutic and Prognostic Implications ," Cancer Res., 67(8):3496-3499 (2007).

Li et al., "Stress Induction of GRP78/BiP and Its Role in Cancer ," Curr. Mol. Med., 6(1):45-54 (2006).

Lou et al., "Endoplasmic Reticulum Stress Involved in Heart and Liver Injury in Iron-Loaded Rats ," Clin Exp Pharmacol Physiol, 36(7):612-618 (2009).

Luo et al., "GRP78/BiP Is Required for Cell Proliferation and Protecting the Inner Cell Mass from Apoptosis during Early Mouse Embryonic Development ," Mol. Cell Biol., 26(15):5688-5697 (2006).

Lye et al., "Subcutaneous Zygomycosis Due to Saksenaea Vasiformis: Rapid Isolate Identification Using a Modified Sporulation Technique," Pathology, 28:364-365 (1996).

Marr et al., "Epidemiology and Outcome of Mould Infections in Hematopoietic Stem Cell Transplant Recipients ," Clin. Infect. Dis., 34(7):909-917 (2002).

Misra et al., "A novel receptor function for the heat shock protein Grp78: silencing of Grp78 gene expression attenuates a2M*-induced signalling ," Cell Signal, 16(8):929-938 (2004).

Morris et al., "Immunoglobulin Binding Protein (BiP) Function Is Required to Protect Cells from Endoplasmic Reticulum Stress but Is Not Required for the Secretion of Selective Proteins ," J. Biol. Chem., 272(7):4327-4334 (1997).

Mote et al., "Glucose regulation of GRP78 gene expression ," Mech Ageing Dev., 104(2):149-158 (1998).

Ni et al., "ER chaperones in mammalian development and human diseases," FEBS Letter, 581(19):3461-3651 (2007).

Pachi et al., "A Randomized, Blinded, Multicenter Trial of Lipid-Associated Amphotericin B Alone versus in Combination with an Antibody-Based Inhibitor of Heat Shock Protein 90 in Patients with Invasive Candidiasis ," Clin. Infect. Dis., 42:1404-1413 (2006).

Phan et al., "N-cadherin Mediates Endocytosis of Candida albicans by Endothelial Cells," J. Biol. Chem., 280(11):10455-10461 (2005).

Reddy et al., "Endoplasmic Reticulum Chaperone Protein GRP78 Protects Cells from Apoptosis Induced by Topoisomerase Inhibitors ," J. Biol. Chem., 278(23)20915-20924 (2003).

Reed et al., "Combination Polyene-Caspofungin Treatment of Rhino-Orbital-Cerebral Mucormycosis," Clin. Infect. Dis., 47(3):364-371 (2008).

Ribes et al., "Zygomycetes in Human Disease," Clin. Microbiol. Rev., 13:236-301 (2000).

Roden et al., "Epidemiology and Outcome of Zygomycosis: A Review of 929 Reported Cases," Clin. Infect. Dis., 41(5):634-653 (2005).

Spellberg et al., "Novel Perspectives on Mucormycosis: Pathophysiology, Presentation, and Management," Clin. Microbiol. Rev., 18:556-569 (2005).

(56) References Cited

OTHER PUBLICATIONS

Spellberg et al., "Efficacy of the Anti-Candida rAls3p-N or rAls1p-N Vaccines against Disseminated and Mucosal Candidiasis," J. Infect. Dis., 194(2):256-260 (2006).

Sugar, A.M., Agent of Mucormycosis and Related Species, pp. 2311-2321 (1995).

Triantafilou et al., "GRP78, a Coreceptor for Coxsackievirus A9, Interacts with Major Histocompatibility Complex Class I Molecules Which Mediate Virus Internalization," J. Virol., 76(2):633-643 (2002).

Van Campenhout et al., "Transferrin Modifications and Lipid Peroxidation: Implications in *Diabetes mellitus*," Free Radic Res., 37(10):1069-1077 (2003).

Ventura et al., "Pneumonia with Cunninghamella Species in Patients with Hematologic Malignancies," Cancer, 58:1534-1536 (1986).

Waldorf et al., "Specific Susceptibility to Mucormycosis in Murine Diabetes and Bronchoalveolar Macrophage Defense against Rhizopus," Journal of Clinical Investigation, 74:150-160 (1984).

Wang et al., "Role of the Unfolded Protein Response Regulator GRP78=BiP in Development, Cancer, and Neurological Disorders," Antioxid Redox Signal., 11(9):2307-2316 (2009).

Websters II New Riverside University Dictionary. The Riverside Publishing Company, p. 933 (1984).

Yu et al., "The Endoplasmic Reticulum Stress-Responsive Protein GRP78 Protects Neurons Against Excitotoxicity and Apoptosis: Suppression of Oxidative Stress and Stabilization of Calcium Homeostasis," Exp. Neurol., 155(2):302-314 (1999).

\* cited by examiner

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cttgttggtg gctcgactcg a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caacaagatg aagagcacca a                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggaaagaagg ttacccatgc                                                20

<210> SEQ ID NO 4
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 4
agaagagaca catcgaaggt                                                   20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
accatcttcc aggagcgag                                                    19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
taagcagttg gtggtgcag                                                    19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcttgccatt caaggtggtt g                                                 21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttctttccca aatacgcctc ag                                                22
```

MAMMALIAN RECEPTORS AS TARGETS FOR ANTIBODY AND ACTIVE VACCINATION THERAPY AGAINST MOLD INFECTIONS

This application is a continuation of U.S. non-provisional patent application Ser. No. 12/874,126, filed Sep. 1, 2010, now abandoned, which claims the benefit of priority to the U.S. provisional patent application Ser. No. 61/239,026, filed Sep. 1, 2009, which are herein incorporated by reference in their entirety.

This invention was made in part with U.S. Government support under NIH grant 011671 awarded by NIAID. The U.S. Government can have certain rights in the invention.

BACKGROUND OF THE INVENTION

The instant application contains a Sequence Listing which has been submitted in ASCII format via EFS-Web and is hereby incorporated by reference in its entirety. Said ASCII copy, created on Dec. 23, 2013, is named 12959-063-999_Sequence_Listing.txt and is 2,256 bytes in size.

This invention generally relates to compositions and methods for treating and preventing infectious diseases in a patient and, more particularly, relates to compositions and methods using antibodies, antibody fragments, small interfering RNAs or vaccines for treating and preventing opportunistic fungal diseases.

About 180 of the 250,000 known fungal species are recognized to cause disease (mycosis) in man and animal. Some of fungi can establish an infection in all exposed subjects, e.g., the systemic pathogens *Histoplasma capsulatum* and *Coccidioides immitis*. Others, such as *Candida, Asergillus* species and Zygomycetes are opportunist pathogens which ordinarily cause disease only in a compromised host. Fungi of the class Zygomycetes, order Mucorales, can cause Mucormycosis, a potentially deadly fungal infection in human. Fungi belonging to the order Mucorales are distributed into at least six families, all of which can cause mucormycosis (Ibrahim et al. *Zygomycosis*, p. 241-251, In W. E. Dismukes, P. G. Pappas, and J. D. Sobel (ed.), *Clinical Mycology*, Oxford University Press, New York (2003); Kwon-Chung, K. J., and J. E. Bennett, *Mucormycosis*, p. 524-559, *Medical Mycology*, Lea & Febiger, Philadelphia (1992), and Ribes et al. *Zygomycetes in Human Disease, Clin Microbiol Rev* 13:236-301 (2000)). However, fungi belonging to the family Mucoraceae, and specifically the species *Rhizopus oryzae* (*Rhizopus arrhizus*), are by far the most common cause of infection (Ribes et al., supra). Increasing cases of mucormycosis have been also reported due to infection with *Cunninghamella* spp. in the Cunninghamellaceae family (Cohen-Abbo et al., *Clinical Infectious Diseases* 17:173-77 (1993); Kontoyianis et al., *Clinical Infectious Diseases* 18:925-28 (1994); Kwon-Chung et al., *American Journal of Clinical Pathology* 64:544-48 (1975), and Ventura et al., *Cancer* 58:1534-36 (1986)). The remaining four families of the Mucorales order are less frequent causes of disease (Bearer et al., *Journal of Clinical Microbiology* 32:1823-24 (1994); Kamalam and Thambiah, *Sabouraudia* 18:19-20 (1980); Kemna et al., *Journal of Clinical Microbiology* 32:843-45 (1994); Lye et al., *Pathology* 28:364-65 (1996), and Ribes et al., (supra)).

The agents of mucormycosis almost uniformly affect immunocompromised hosts (Spellberg et al., *Clin. Microbiol. Rev.* 18:556-69 (2005)). The major risk factors for mucormycosis include uncontrolled diabetes mellitus in ketoacidosis known as diabetes ketoacidosis (DKA), other forms of metabolic acidosis, treatment with corticosteroids, organ or bone marrow transplantation, neutropenia, trauma and burns, malignant hematological disorders, and deferoxamine chelation-therapy in subjects receiving hemodialysis.

Recent reports have demonstrated a striking increase in the number of reported cases of mucormycosis over the last two decades (Gleissner et al., *Leuk. Lymphoma* 45(7):1351-60 (2004)). There has also been an alarming rise in the incidence of mucormycosis at major transplant centers. For example, at the Fred Hutchinson Cancer Center, Marr et al. have described a greater than doubling in the number of cases from 1985-1989 to 1995-1999 (Marr et al., *Clin. Infect. Dis.* 34(7): 909-17 (2002)). Similarly, Kontoyiannis et al. have described a greater than doubling in the incidence of mucormycosis in transplant subjects over a similar time-span (Kontoyiannis et al, *Clin. Infect. Dis.* 30(6):851-6 (2000)). Given the increasing prevalence of diabetes, cancer, and organ transplantation in the aging United States population, the rise in incidence of mucormycosis is anticipated to continue unabated for the foreseeable future.

Available therapies for invasive mucormycosis include attempts to reverse the underlying predisposing factors, emergent, wide-spread surgical debridement of the infected area, and adjunctive antifungal therapy (Edwards, J., Jr., Zygomycosis, p. 1192-1199. In P. Hoeprich and M. Jordan (ed.), *Infectious Disease*, 4th ed. J.B. Lippincott Co., Philadelphia (1989); Ibrahim et al., (2003), supra; Kwon-Chung and Bennett, supra; Sugar, A. M., Agent of Mucormycosis and Related Species, p. 2311-2321. In G. Mandell, J. Bennett, and R. Dolin (ed.), *Principles and Practices of Infectious Diseases*, 4th ed. Churchill Livingstone, N.Y. (1995)).

Currently, Amphotericin B (AmB) remains the only antifungal agent approved for the treatment of invasive mucormycosis (Id.). Because the fungus is relatively resistant to AmB, high doses are required, which frequently cause nephrotoxicity and other adverse effects (Sugar, supra). Also, in the absence of surgical removal of the infected focus (such as excision of the eye in subjects with rhinocerebral mucormycosis), antifungal therapy alone is rarely curative (Edwards, J. (1989), supra; Ibrahim et al., (2003), supra). Even when surgical debridement is combined with high-dose AmB, the mortality associated with mucormycosis exceeds 50% (Sugar, supra). In subjects with disseminated disease mortality approaches 100% (Husain et al., *Clin Infect Dis* 37:221-29 (2003)). Because of this unacceptably high mortality rate, and the extreme morbidity of highly disfiguring surgical therapy, it has been imperative to develop new strategies to treat and prevent invasive mucormycosis.

A hallmark of mucormycosis is the virtually uniform presence of extensive angioinvasion with resultant vessel thrombosis and tissue necrosis (Ibrahim et al., (2003), supra. and Spellberg et al., (2005), supra.) This angioinvasive character is associated with the ability of the organism to hematogenously disseminate to other target organs. Furthermore, ischemic necrosis of infected tissues as a result of fungal angioinvasion can prevent delivery of adequate levels of antifungal therapies, and is likely an important mechanism by which the fungus survives despite therapy with fungicidal agents. For these reasons, damage of and penetration through endothelial cells lining blood vessels is likely a critical step in *R. oryzae*'s pathogenetic strategy. *R. oryzae* spores and hyphae have been shown to damage human umbilical vein endothelial cells in vitro (Ibrahim et al., *Infect Immun* 73(2): 778, (2005)). Such injury requires adherence of the fungus to endothelial cells followed by invasion into the cells. Adherence to endothelial cells is believed to be mediated by a specific receptor since it was found to be saturable (Ibrahim et al., *Infect Immun* 73(2):778, (2005)).

Therefore, there exists a need for compounds and methods that can reduce the risk of mucormycosis pathogenesis and provide effective therapies without adverse effects. The present invention satisfies this need and provides related advantages as well.

SUMMARY OF THE INVENTION

In accordance with the embodiments outlined in this disclosure, the present invention provides pharmaceutical compositions for treating or preventing a fungal condition in a subject in need thereof, having an antibody or antibody fragment thereof that specifically binds to a GRP78 polypeptide or a fragment thereof; and a pharmaceutically acceptable excipient or carrier.

In another embodiment, the present invention provides pharmaceutical compositions for treating or preventing a fungal condition in a subject in need thereof, having a small interfering RNA composed of the nucleotide sequence CTTGTTGGTGGCTCGACTCGA (SEQ ID NO. 1); and a pharmaceutically acceptable excipient or carrier.

In another embodiment, the present invention provides vaccine compositions for immunization of a subject against a fungal condition, having a GRP78 polypeptide, or an antigenic fragment of said polypeptide, and a pharmaceutically acceptable carrier.

In another embodiment, the present invention provides methods of treating or preventing a fungal condition by administering to a subject having, or susceptible to having, a fungal condition a therapeutically effective amount of an antibody or antibody fragment thereof that specifically binds to a GRP78 polypeptide or a fragment thereof.

In another embodiment, the present invention provides methods of treating or preventing a fungal condition by administering to a subject having, or susceptible to having, a fungal condition an immunogenic amount of a GRP78 polypeptide, or an immunogenic fragment thereof.

In another embodiment, the present invention provides methods of treating or preventing a fungal condition by administering to a subject having, or susceptible to having, a fungal condition a therapeutically effective amount of a small interfering RNA composed of the nucleotide sequence CTTGTTGGTGGCTCGACTCGA (SEQ ID NO. 1).

DETAILED DESCRIPTION OF THE INVENTION

Figure 1:
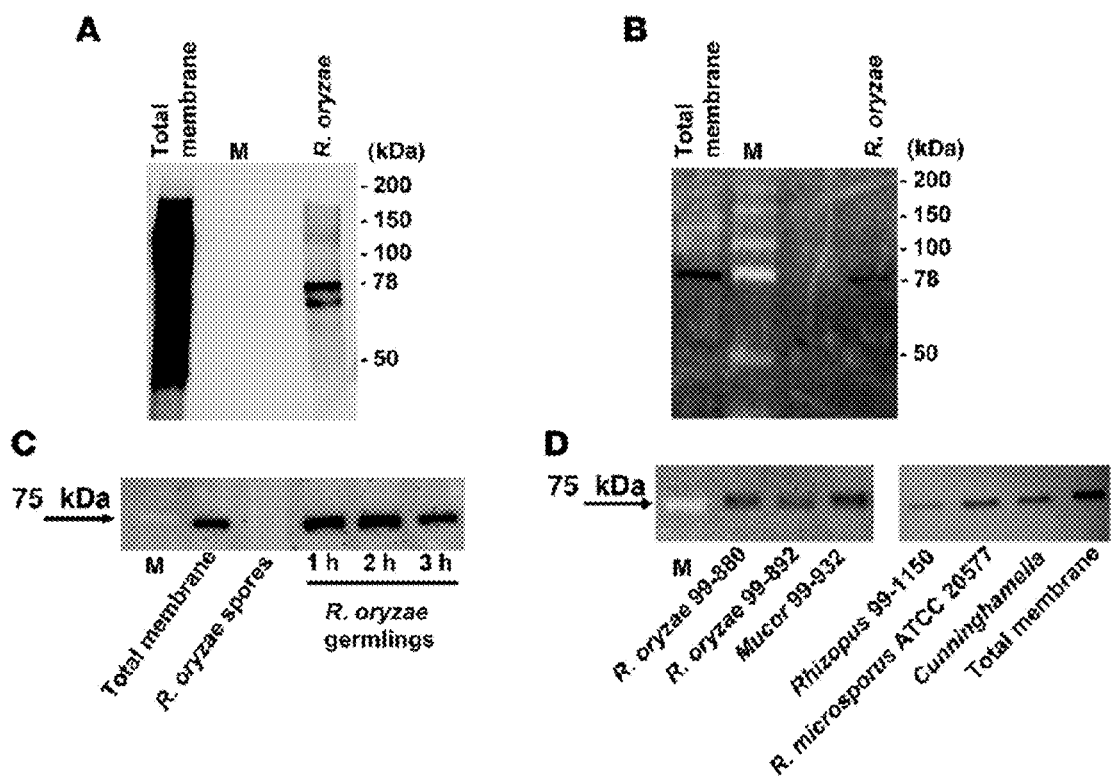
FIG. 1, panels A-D, show endothelial cell surface GRP78 binds to Mucorales germlings. Panel A) Endothelial cell surface proteins were labeled with NHS-biotin as described in Isberg and Leong, Cell 60(5):861 (1990) and then extracted with n-octyl-β-D-glucopyranoside in PBS containing $Ca^{2+}$ and $Mg^{2+}$ and protease inhibitors. The labeled proteins (250 µg) were incubated with equal volumes of spores ($8\times10^8$) or germlings ($2\times10^8$) of R. oryzae followed by extensive rinsing with PBS containing $Ca^{2+}$ and $Mg^{2+}$ to remove the unbound proteins. The membrane proteins that remained bound to the organisms were eluted with 6M urea, separated on 10% SDS-PAGE, and identified by immunoblotting with an anti-biotin monoclonal Ab. Proteins from another SDS-PAGE were stained with SYPRO Ruby and the bands excised for sequencing. Panel B) The same membrane that was probed with anti-biotin Ab (Panel A) was stripped and then probed with anti-GRP78 Ab. Panel C) R. oryzae spores were germinated as described in Ibrahim et al., Infect Immun 73(2):778 (2005) at different time intervals and assayed for binding to endothelial cell surface protein. Immunoblotting against anti-GRP78 Ab was carried out as in panels A and B. Panel D) An immunoblot of endothelial cell surface proteins bound to different Mucorales was developed with an anti-GRP78 Ab. "Total membrane" refers to total endothelial cell membrane proteins. "M" refers to molecular weight marker.

This invention is directed to the use of compositions and methods that directly and/or indirectly inhibit the GRP78 polypeptide which facilitates fungal-induced penetration and subsequent damage of endothelial cells, specifically those involved in the onset of mucormycosis. Expression of the GRP78 polypeptide is described herein to be enhanced in the presence of elevated glucose and iron levels, consistent with typical levels seen in patients suffering from diabetic ketoacidosis (DKA). Enhanced GRP78 expression results in increased endocytosis and subsequent damage to endothelial cells Inhibition of the GRP78 polypeptide, described herein, impedes the ability of the fungi to penetrate and subsequently damage endothelial cells. Therefore, the compositions and methods of the current invention in targeting and inhibiting the GRP78 polypeptide will prevent fungal-induced penetration and subsequent damage of endothelial cells, which constitutes an effective and targeted therapy against fungal conditions.

In one embodiment, the invention is directed to a pharmaceutical composition for treating or preventing a fungal condition. The pharmaceutical composition includes an effective dose of an antibody or antibody fragment thereof that specifically binds to a GRP78 polypeptide. In one aspect, the pharmaceutical composition of the invention inhibits the receptor activity of GRP78, thereby preventing penetration through and damage of endothelial cells by a fungus. In another aspect, a composition of the invention further comprises a pharmaceutically acceptable excipient or carrier.

In another embodiment, the invention is directed to an immunogenic composition such as a vaccine. The immunogenic composition includes an effective dose of GRP78 polypeptide or an antigenic fragment thereof that confers protection against a fungal condition in a subject. The vaccine composition of the invention induces host humoral and/or cell mediated immune response against GRP78 polypeptide. In another embodiment, a composition of the invention further includes an adjuvant that can boost the immunogenicity of the vaccine composition. In a further aspect, the subject is a human.

In yet another embodiment, the invention includes an inhibitor of GRP78 nucleic acid such as an siRNA. The GRP78 inhibitor includes a vector expressing one or more siRNAs that include sequences sufficiently complementary to a portion of the GRP78 nucleic acid for inhibiting GRP78 transcription or translation levels. For example, as described in Example I, interfering RNAs against host GRP78 were prepared, which were shown to inhibit GRP78 expression in endothelial cells and showed a significant reduction in *R. oryzae*-induced endocytosis and subsequent damage. Therefore, in one aspect, the invention provides a pharmaceutical composition for treating or preventing a fungal condition in a subject in need thereof, comprising a small interfering RNA having the nucleotide sequence CTTGTTGGTGGCTC-GACTCGA (SEQ ID NO. 1). In another aspect, a composition of the invention further comprises a pharmaceutically acceptable excipient or carrier.

Generally, nucleic acid is an RNA, for example, mRNA or pre-mRNA, or DNA, such as cDNA and genomic DNA. An GRP78 nucleic acid, for example, refers to a nucleic acid molecule (RNA, mRNA, cDNA, or genomic DNA, either single- or double-stranded) corresponding to GRP78 polypeptide or an immunogenic fragment thereof. DNA molecules can be doubled-stranded or singled-stranded; single stranded RNA or DNA can be either the coding or sense strand, or the non-coding or antisense strand. The nucleic acid molecule or nucleotide sequence can include all or a portion of the coding sequence of the gene and can further include additional non-coding sequences such as introns and non-coding 3' and 5' sequences (including promoter, regulatory, poly-A stretches or enhancer sequences, for example). In addition, the nucleic acid molecule or nucleotide sequence can be fused to another sequence, for example, a label, a marker or a sequence that encodes a polypeptide that assists in isolation or purification of the polypeptide. Such sequences include, but are not limited to, those that encode a selection marker (e.g. an antibiotic resistance gene, or a reporter sequence), those that encode a repetition of histidine (HIS tag) and those that encode a glutathione-S-transferase (GST) fusion protein. The nucleic acid molecule or nucleotide sequence can include a nucleic acid molecule or nucleotide sequence which is synthesized chemically or by recombinant means, such nucleic acid molecule or nucleotide sequence is suitable for use in recombinant DNA processes and within genetically engineered protein synthesis systems.

The term "polypeptide" refers to a chain of two or more amino acids covalently linked by a peptide bond. Particular polypeptides of interest in the context of this invention are amino acid subsequences having antigenic epitopes. Antigenic epitopes are well known in the art and include sequence and/or structural determinants substantially responsible for the immunogenic properties of a polypeptide and being capable of evoking an immune response. Functional domains of the GRP78 polypeptide are also considered to fall within the scope of the invention. Polypeptides also undergo maturation or post-translational modification processes that can include, for example, glycosylation, proteolytic cleavage, lipidization, signal peptide cleavage, propeptide cleavage, phosphorylation, and such like.

GRP78 (also known as: immunoglobulin heavy chain binding protein (BiP); endoplasmic reticulum lumenal Ca(2+)-binding protein grp78; heat shock 70 kDa protein 5 (HSPA5); and heat shock 70 kD protein 5 (glucose-regulated protein, 78 kD)) is a member of the HSP70 protein family that can be located on the cell surface (Wang et al., *Antioxidants & Redox Signaling In Press* (2009)) and is a key regulator of the unfolded protein response (UPR) (Ni and Lee, *FEBS Lett* 581(19):3641 (2007)). GRP78 was discovered as a cellular protein induced by glucose starvation (Lee, *Cancer Res* 67(8):3496 (2007)). GRP78 is present in the endoplasmic reticulum as a major chaperone involved in many cellular processes, including protein folding and assembly, marking misfolded proteins for proteosome degradation, regulating $Ca^{2+}$ homeostasis, and serving as a sensor for endoplasmic reticulum stress (Li and Lee, *Curr Mol Med* 6(1):45 (2006)). Despite its main function as a cellular chaperone protein, recent studies reported the translocation of a fraction of GRP78 to the cell surface in a variety of cells (Davidson et al., *Cancer Res* 65(11):4663 (2005); Misra et al., *Cell Signal* 16(8):929 (2004); Hardy et al., *Biochem Pharmacol* 75(4): 891 (2008); Jindadamrongwech et al., *Arch Virol* 149(5):915 (2004); and Triantafilou et al., *J Virol* 76(2):633 (2002)). The polypeptide sequence of GRP78 has been previously identified and described for several species including *Homo sapiens, Pongo abelii, Pan troglodytes, Mus musculus, Rattus norvegicus, Cricetulus griseus, Bos Taurus, Canis lupus familiaris*, and others. See, for example, the amino acid sequences described by the Nation Center for Biotechnology Information (NCBI) identified by the following accession and gene identification (GI) numbers: NP_005338.1 (GI: 16507237); AAF13605.1 (GI:6470150); NP_005338.1 (GI: 16507237); P11021.2 (GI:14916999); NP_001126927.1 (GI:197101513); NP_001156906.1 (GI:254540168); AAO65155.1 (GI:29164908); A27414 (GI:90188); AAI19954.1 (GI:111308468); XP_537847.2 (GI: 73968072), all of which are herein incorporated by reference. The corresponding nucleic acid cDNA, mRNA or genomic sequences have also been identified and described for the above species as described by NCBI and identified by the following accession and gene identification (GI) numbers: NM_005347.3 (GI:194097371); M19645.1 (GI:183644); AF188611.1 (GI:6470149); AF216292.1 (GI:7229461); NM_001133455.1 (GI:197101512); XM_001146903.1 (GI:114689310); NM_001163434.1 (GI:254540167); NM_022310.3 (GI:254540165); NM_013083.1 (GI: 25742762); M17169.1 (GI:191090); NM_001075148.1 (GI: 115495026); XM_537847.2 (GI:73968071), all of which are herein incorporated by reference.

The term "immunogenic" or "antigenic" as it is used herein refers to a portion of a protein that is recognized by a T-cell and/or B-cell antigen receptor. The immunogenic portion generally includes at least 5 amino acid residues, preferably at least 10, more preferably at least 20, and still more preferably at least 30 amino acid residues of an GRP78 polypeptide or a variant thereof. Preferred immunogenic portions can contain a small N- and/or C-terminal fragment (e.g., 5-30 amino acids, preferably 10-25 amino acids).

A variant polypeptide contains at least one amino acid change compared to the target polypeptide. Polypeptide variants of GRP78 can exhibit at least about 39%, more preferably at least about 50%, and even more preferably at least about 70% identity to the GRP78 polypeptide. A polynucleotide variant includes a substantially homologous polynucleotide that deviates in some bases from the identified polynucleotide, usually caused by mutations such as substitution, insertion, deletion or transposition. Polynucleotide variants preferably exhibit at least about 60% (for fragments with 10 or more nucleotides), more preferably at least about 70%, 80% or 90%, and even more preferably at least about 95%, 98% or 99% identity to the identified polynucleotide.

The term "fragment" as used herein with reference to an GRP78 polypeptide is intended to refer to a polypeptide having a portion of GRP78 amino acid sequence. Useful fragments include those that retain one or more of the biological activities of the polypeptide. Such biologically active fragments can have a wide range of lengths including, for example, 4, 6, 10, 15, 20, 25, 30, 40, 50, 100, or more amino acid in length. In addition to activity, biologically active fragments also can be characterized by, for example, a motif, domain, or segment that has been identified by analysis of the polypeptide sequence using methods well known in the art. Such regions can include, for example, a signal peptide, extracellular domain, transmembrane segment, ligand binding region, zinc finger domain and/or glycosylation site.

The term "vaccine", as used herein, refers to a composition that can be administered to an individual to protect the individual against an infectious disease. Vaccines protect against diseases by inducing or increasing an immune response in an animal against the infectious disease. An exemplary infectious disease amenable to treatment with the vaccines of the invention is mucormycosis. The vaccine-mediated protection can be humoral and/or cell mediated immunity induced in host when a subject is challenged with, for example, GRP78 or an immunogenic portion or fragment thereof.

The term "adjuvant" is intended to mean a composition with the ability to enhance an immune response to an antigen generally by being delivered with the antigen at or near the site of the antigen. Ability to increase an immune response is manifested by an increase in immune mediated protection. Enhancement of humoral immunity can be determined by, for example, an increase in the titer of antibody raised to the antigen. Enhancement of cellular immunity can be measured by, for example, a positive skin test, cytotoxic T-cell assay, ELISPOT assay for IFN-gamma or IL-2. Adjuvants are well known in the art. Exemplary adjuvants include, for example, Freud's complete adjuvant, Freud's incomplete adjuvant, aluminum adjuvants, MF59 and QS21.

The term "antibody" as used herein refers to immunoglobulin molecules and immunologically active portion of immunoglobulin molecules. Antibodies can be prepared by any of a variety of techniques known to those skilled in the art (see, for example, Harlow and Lane, *Antibodies: A Laboratory Manual*, Cold Spring Harbor Laboratories, Cold Spring Harbor, N.Y., 1988 and Brekke and Sandlie, Therapeutic Antibodies for Human Diseases at the Dawn of the Twenty-First Century, *Nature* 52(2):52-62 (2003)). The present invention provides polyclonal and monoclonal antibodies that bind specifically to a polypeptide of the invention or fragment or variant thereof. Monoclonal antibodies of the invention, for example, include a population of antibody molecules that contain only one species of antigen binding site capable of immunoreacting with a particular epitope of a polypeptide of the invention or a fragment or variant thereof. Monoclonal antibodies can be coupled to one or more therapeutic agents. Suitable agents in this regard include differentiation inducers, drugs, toxins, and derivatives thereof. A therapeutic agent can be coupled (e.g., covalently bonded) to a suitable monoclonal antibody either directly or indirectly (e.g., via a linker group).

The terms "vector", "cloning vector" and "expression vector" mean the vehicle by which a nucleic acid can be introduced into a host cell. The vector can be used for propagation or harboring a nucleic acid or for polypeptide expression of an encoded sequence. A wide variety of vectors are known in the art and include, for example, plasmids, phages and viruses. Exemplary vectors can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999).

The term "treating" or "treatment," as it is used herein is intended to mean an amelioration of a clinical symptom indicative of a fungal condition. Amelioration of a clinical symptom includes, for example, a decrease or reduction in at least one symptom of a fungal condition in a treated individual compared to pretreatment levels or compared to an individual with a fungal condition. The term "treating" also is intended to include the reduction in severity of a pathological condition, a chronic complication or an opportunistic fungal infection which is associated with a fungal condition. Such pathological conditions, chronic complications or opportunistic infections are exemplified below with reference to mucormycosis. Mucormycosis and other such pathological conditions, chronic complications and opportunistic infections also can be found described in, for example, Merck Manual, Sixteenth Edition, 1992, and Spellberg et al., *Clin. Microbio. Rev.* 18:556-69 (2005).

The term "preventing" or "prevention," as it is used herein is intended to mean a forestalling of a clinical symptom indicative of a fungal condition. Such forestalling includes, for example, the maintenance of normal physiological indicators in an individual at risk of infection by a fungus or fungi prior to the development of overt symptoms of the condition or prior to diagnosis of the condition. Therefore, the term "preventing" includes the prophylactic treatment of individuals to guard them from the occurrence of a fungal condition. Preventing a fungal condition in an individual also is intended to include inhibiting or arresting the development of the fungal condition Inhibiting or arresting the development of the condition includes, for example, inhibiting or arresting the occurrence of abnormal physiological indicators or clinical symptoms such as those described above and/or well known in the art. Therefore, effective prevention of a fungal condition would include maintenance of normal body temperature, weight, psychological state as well as lack of lesions or other pathological manifestations in an individual predisposed to a fungal condition. Individuals predisposed to a fungal condition include an individual who is immunocompromised, for example, but not limited to, an individual with AIDS, azotemia, diabetes mellitus, diabetic ketoacidosis, neutropenia, bronchiectasis, emphysema, TB, lymphoma, leukemia, or burns, or an individual undergoing chemotherapy, bone marrow-, stem cell- and/or solid organ transplantation or an individual with a history of susceptibility to a fungal condition Inhibiting or arresting the development of the condition also includes, for example, inhibiting or arresting the progression of one or more pathological conditions, chronic complications or susceptibility to an opportunistic infection associated with a fungal condition.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

The term "fungal condition" as used herein refers to fungal diseases, infection, or colonization including superficial mycoses (i.e., fungal diseases of skin, hair, nail and mucous membranes; for example, ringworm or yeast infection), subcutaneous mycoses (i.e., fungal diseases of subcutaneous tissues, fascia and bone; for example, mycetoma, chromomycosis, or sporotichosis), and systemic mycoses (i.e., deep-seated fungal infections generally resulting from the inhalation of air-borne spores produced by causal moulds; for example, zygomycosis, aspergillosis, cryptococcosis, candidiasis, histoplasmosis, coccidiomycosis, paracoccidiomycosis, fusariosis (hyalohyphomycoses), blastomycosis, penicilliosis or sporotrichosis.

As used herein, the term "zygomycosis" is intended to mean a fungal condition caused by fungi of the class Zygomycetes, comprised of the orders Mucorales and Entomophthorales. The Entomophthorales are causes of subcutaneous and mucocutaneous infections known as entomophthoromycosis, which largely afflict immunocompetent hosts in developing countries. Zygomycosis is also referred to as mucormycosis and the two terms are used interchangeably to refer to similar types of fungal infections.

As used herein, the term "mucormycosis" is intended to mean a fungal condition caused by fungi of the order Mucorales. Mucormycosis is a life-threatening fungal infection almost uniformly affecting immunocompromised hosts in either developing or industrialized countries. Fungi belonging to the order Mucorales are distributed into at least six families, all of which can cause cutaneous and deep infections. Species belonging to the family Mucoraceae are isolated more frequently from patients with mucormycosis than any other family. Among the Mucoraceae, *Rhizopus oryzae* (*Rhizopus arrhizus*) is a common cause of infection. Other exemplary species of the Mucoraceae family that cause a similar spectrum of infections include, for example, *Rhizopus microsporus* var. *rhizopodiformis*, *Absidia corymbifera*, *Apophysomyces elegans*, *Mucor* species, *Rhizomucor pusillus* and *Cunninghamella* spp (Cunninghamellaceae family). Mucormycosis is well known in the art and includes, for example, rinocerebral mucormycosis, pulmonary mucormycosis, gastrointestinal mucormycosis, disseminated mucormycosis, bone mucormycosis, mediastinum mucormycosis, trachea mucormycosis, kidney mucormycosis, peritoneum mucormycosis, superior vena cava mucormycosis or external otitis mucormycosis.

Fungi belonging to the order Mucorales are currently distributed into the families of Choanephoraceae; Cunninghamellaceae; Mucoraceae; Mycotyphaceae; Phycomycetaceae; Pilobolaceae; Saksenaeaceae; Syncephalastraceae; and Umbelopsidaceae. Each of these fungi families consists of one or more genera. For example, fungi belonging to the order Mucorales, family Mucoraceae, are further classified into the genera of *Absidia* (e.g., *A. corymbifera*); *Actinomucor* (e.g., *A. elegans*); *Amylomyces* (e.g., *A. rouxii*); *Apophysomyces*; *Backusella* (e.g., *B. circina*); *Benjaminiella* (e.g., *B. multispora*); *Chaetocladium* (e.g., *C. brefeldii*); *Circinella* (e.g., *C. angarensis*); *Cokeromyces* (e.g., *C. recurvatus*); *Dicranophora* (e.g., *D. fulva*); *Ellisomyces* (e.g., *E. anomalus; Helicostylum* (e.g., *H. elegans*); *Hyphomucor* (e.g., *H. assamensis*); *Kirkomyces* (e.g., *K. cordensis*); *Mucor* (e.g., *M. amphibiorum*); *Parasitella* (e.g., *P. parasitica*); *Philophora* (e.g., *P. agaricine*); *Pilaira* (e.g., *P. anomala*); *Pirella* (e.g., *P. circinans*); *Rhizomucor* (e.g., *R. endophyticus*); *Rhizopodopsis* (e.g., *R. javensis*); *Rhizopus*; *Sporodiniella* (e.g., *S. umbellata*); *Syzygites* (e.g., *S. megalocarpus*); *Thamnidium* (e.g., *T. elegans*); *Thermomucor* (e.g., *T. indicae-seudaticae*); and *Zygorhynchus* (e.g., *Z. californiensis*). The genus *Rhizopus*, for example, consists of *R. azygosporus; R. caespitosus; R. homothallicus; R. oryzae; R. microsporus, R. microsporus* var. *rhizopodiformis* and *R. schipperae* species.

The Choanephoraceae family consists of fungi genera *Blakeslea* (e.g., *B. monospora*), *Choanephora* (e.g., *C. cucurbitarum*), *Gilbertella* (e.g., *G. hainanensis*), and *Poitrasia* (e.g., *P. circinans*). The Cunninghamellaceae family consists of genera *Chlamydoabsidia* (e.g., *C. padenii*); *Cunninghamella* (e.g., *C. antarctica*); *Gongronella* (e.g., *G. butleri*); *Halteromyces* (e.g., *H. radiatus*); and *Hesseltinella* (e.g., *H. vesiculosa*). The Mycotyphaceae family consists of fungi genus *Mycotypha* (e.g., *M. africana*). The Phycomycetaceae family consists of fungi genus *Phycomyces* (e.g., *P. blakesleeanus*) and *Spinellus* (e.g., *S. chalybeus*). The Pilobolaceae family consists of fungi genera *Pilobolus* (e.g., *P. longipes*) and *Utharomyces* (e.g., *U. epallocaulus*). The Saksenaeaceae family consists of fungi genera *Apophysomyces* (e.g., *A. elegans*) and Saksenaea (e.g., *S. vasiformis*). The Syncephalastraceae family consists of fungi genera *Dichotomocladium* (e.g., *D. elegans*); *Fennellomyces* (e.g., *F. gigacellularis*); *Mycocladus* (e.g., *M. blakesleeanus*); *Phascolomyces* (e.g., *P. articulosus*); *Protomycocladus* (e.g., *P. faisalabadensis*); *Syncephalastrum* (e.g., *S. monosporum*); *Thamnostylum* (e.g., *T. lucknowense*); *Zychaea* (e.g., *Z. mexicana*). Finally, the Umbelopsidaceae family consists of fungi genus *Umbelopsis* (e.g., *U. angularis*).

As used herein, the term "pharmaceutically acceptable carrier" includes any and all pharmaceutical grade solvents, buffers, oils, lipids, dispersion media, coatings, isotonic and absorption facilitating agents and the like that are compatible with the active ingredient. These pharmaceutically acceptable carriers can be prepared from a wide range of pharmaceutical grade materials appropriate for the chosen mode of administration, e.g., injection, intranasal administration, oral administration, etc. For the purposes of this invention, the terms "pharmaceutical" or "pharmaceutically acceptable" further refer to compositions formulated by known techniques to be non-toxic and, when desired, used with carriers or additives that can be safely administered to humans. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "immunogenic amount" as used herein refers an effective amount of a particular epitope of a polypeptide of the invention or a fragment or variant thereof that can induce the host immune response against the polypeptide or the infectious agent expressing the polypeptide. This amount is generally in the range of 20 µg to 10 mg of antigen per dose of vaccine and depends on the subject to be treated, capacity of the subject's immune system to synthesize antibodies, and the degree of protection desired. The precise amount of immunogen required can be calculated by various methods such as, for example, antibody titration. The term effective amount refers to an amount of a compound or compositions that is sufficient to provide a desired result. Thus, as used to describe a vaccine, an effective amount refers to an amount of a compound or composition (e.g., an antigen) that is sufficient to produce or elicit a protective immune response. An effective amount with respect to an immunological composition is an amount that is sufficient to elicit an immune response, whether or not the response is protective.

The "therapeutically effective amount" will vary depending on the polypeptide, polynucleotide, antibody, antibody fragment or compositions, the disease and its severity and the age, weight, etc., of the patient to be treated all of which is within the skill of the attending clinician. It is contemplated that a therapeutically effective amount of one or more of a polynucleotide, polypeptide, antibody, antibody fragment or composition described herein will alter a fungal pathogen penetration through and damage of endothelial cells in the patient as compared to the absence of treatment. As such, fungal pathogenesis is decreased. A therapeutically effective amount is distinguishable from an amount having a biological effect (a "biologically effective amount"). A polypeptide, polynucleotide, antibody, antibody fragment or compositions of the present invention may have one or more biological effects in vitro or even in vivo, such as reducing function of a GRP78 polypeptide. A biological effect, however, may not result in any clinically measurable therapeutically effect as described herein as determined by methods within the skill of the attending clinician.

The present invention, in part, relates to the discovery that GRP78 gene product is overexpressed in the presence of elevated concentrations of glucose and iron and mediates penetration through and damage of endothelial cells by a fungal pathogen such as R. oryzae in mucormycosis. Moreover, inhibition of GRP78 polypeptide protected subjects from mucormycosis, particular those suffering from diabetic ketoacidosis.

Accordingly, different compositions are disclosed herein for effective inhibition of GRP78 polypeptide, GRP78 nucleic acid and/or its function in treating mucormycosis or other fungal diseases. These inhibitory compositions include vaccines, antisense, siRNA, antibody or any other compositions capable of effectively targeting and inhibiting the function of GRP78 polypeptide. Such compositions will reduce and/or prevent the growth of the fungus in the infected tissues. The compositions of the invention also are useful in prophylactic settings to decrease onset and/or prevent infection from occurring. In addition, any of the GRP78 inhibitory compositions disclosed herein can further be supplemented and/or combined with other known antifungal therapies including, for example, Amphotericin B or iron chelators. Exemplary iron chelators include Deferiprone and Deferasirox.

In one embodiment, the invention provides a vaccine composition having a GRP78 polypeptide or an antigenic fragment or variant of the polypeptide. The vaccine composition also can include an adjuvant. The formulation of the vaccine composition of the invention is effective in inducing protective immunity in a subject by stimulating both specific humoral (neutralizing antibodies) and effector cell mediated immune responses against GRP78 polypeptide. The vaccine composition of the invention is also used in the treatment or prophylaxis of fungal infections such as, for example, mucormycosis.

The vaccine of the present invention will contain an immunoprotective quantity of GRP78 polypeptide antigens and is prepared by methods well known in the art. The preparation of vaccines is generally described in, for example, M. F. Powell and M. J. Newman, eds., "Vaccine Design (the subunit and adjuvant approach)," Plenum Press (1995); A. Robinson, M. Cranage, and M. Hudson, eds., "Vaccine Protocols (Methods in Molecular Medicine)," Humana Press (2003); and D. Ohagan, ed., "Vaccine Adjuvants: Preparation Methods and Research Protocols (Methods in Molecular Medicine)," Humana Press (2000).

GRP78 polypeptide, and peptide fragments or variants thereof can include immunogenic epitopes, which can be identified using methods known in the art and described in, for example, Geysen et al. Proc. Natl. Acad. Sci. USA 81: 3998 (1984)). Briefly, hundreds of overlapping short peptides, e.g., hexapeptides, can be synthesized covering the entire amino acid sequence of the target polypeptide (i.e., GRP78). The peptides while still attached to the solid support used for their synthesis are then tested for antigenicity by an ELISA method using a variety of antisera. Antiserum against GRP78 protein can be obtained by known techniques, Kohler and Milstein, Nature 256: 495-499 (1975), and can be humanized to reduce antigenicity, see, for example, U.S. Pat. No. 5,693,762, or produced in transgenic mice leaving an unrearranged human immunoglobulin gene, see, for example, U.S. Pat. No. 5,877,397. Once an epitope bearing hexapeptide reactive with antibody raised against the intact protein is identified, the peptide can be further tested for specificity by amino acid substitution at every position and/or extension at both C and/or N terminal ends. Such epitope bearing polypeptides typically contain at least six to fourteen amino acid residues, and can be produced, for example, by polypeptide synthesis using methods well known in the art or by fragmenting an GRP78 polypeptide. With respect to the molecule used as immunogens pursuant to the present invention, those skilled in the art will recognize that the GRP78 polypeptide can be truncated or fragmented without losing the essential qualities as an immunogenic vaccine. For example, GRP78 polypeptide can be truncated to yield an N-terminal fragment by truncation from the C-terminal end with preservation of the functional properties of the molecule as an immunogen. Similarly, C-terminal fragments can be generated by truncation from the N-terminal end with preservation of the functional properties of the molecule as an immunogen. Other modifications in accord with the teachings and guidance provided herein can be made pursuant to this invention to create other GRP78 polypeptide functional fragments, immunogenic fragments, variants, analogs or derivatives thereof, to achieve the therapeutically useful properties described herein with the native protein.

The vaccine compositions of the invention further contain conventional pharmaceutical carriers. Suitable carriers are well known to those of skill in the art. These vaccine compositions can be prepared in liquid unit dose forms. Other optional components, e.g., pharmaceutical grade stabilizers, buffers, preservatives, excipients and the like can be readily selected by one of skill in the art. However, the compositions can be lyophilized and reconstituted prior to use. Alternatively, the vaccine compositions can be prepared in any manner appropriate for the chosen mode of administration, e.g., intranasal administration, oral administration, etc. The preparation of a pharmaceutically acceptable vaccine, having due regard to pH, isotonicity, stability and the like, is within the skill of the art.

The immunogenicity of the vaccine compositions of the invention can further be enhanced if the vaccine further comprises an adjuvant substance. Various methods of achieving adjuvant effect for the vaccine are known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generationn Immunological Adjuvants", 1995, Gregoriadis G et al. (eds.), Plenum Press, New York, ISBN 0-306-45283-9, both of which are hereby incorporated by reference herein.

Preferred adjuvants facilitate uptake of the vaccine molecules by antigen presenting cells (APCs), such as dendritic cells, and activate these cells. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM® matrix); a particle; DDA (dimethyldioctadecylammonium bromide); aluminium adjuvants; DNA adjuvants; and an encapsulating adjuvant. Liposome formulations are also known to confer adjuvant effects, and therefore liposome adjuvants are included according to the invention.

In addition to vaccination of subjects susceptible to fungal infections such as mucormycosis, the vaccine compositions of the present invention can be used to treat, immunotherapeutically, subjects suffering from a variety of fungal infections. Accordingly, vaccines that contain one or more of GRP78 polynucleotides, polypeptides and/or antibody compositions described herein in combination with adjuvants, and that act for the purposes of prophylactic or therapeutic use, are also within the scope of the invention. In an embodiment, vaccines of the present invention will induce the body's own immune system to seek out and inhibit GRP78 molecules.

In another embodiment, the invention provides a pharmaceutical composition for treating or preventing a fungal condition having an antisense or a small interfering RNA selected from the group consisting of a nucleotide sequence that is substantially complimentary to a portion of an GRP78 nucleic acid sequence; a nucleotide sequence that is substantially complimentary to at least 12 contiguous nucleotide bases of GRP78 sequence; a nucleotide RNAi sequence that is substantially complimentary to at least 18 contiguous nucleotide bases of GRP78 sequence; and a pharmaceutically acceptable excipient or carrier. In one aspect, the small interfering RNA includes the nucleotide sequence CTTGTTGGTGGCTCGACTCGA (SEQ ID NO. 1). In another aspect, the pharmaceutical composition further includes an adjuvant.

Antisense nucleic acid molecules of the invention can be designed using the nucleotide sequences of the GRP78 genes identified herein or their complementary strands thereof, and/or a portion or variant thereof, constructed using enzymatic ligation reactions by procedures known in the art of genetic engineering. For example, an antisense nucleic acid molecule (e.g., an antisense oligonucleotide) can be chemically synthesized using naturally occurring nucleotides or variously modified nucleotides designed to hybridize with a control region of a gene (e.g., promoter, enhancer, or transcription initiation region) to inhibit the expression of the GRP78 gene through triple-helix formation. Alternatively, the antisense nucleic acid molecule can be designed to hybridize with the transcript of a gene (i.e., mRNA), and thus inhibit the translation of GRP78 by inhibiting the binding of the transcript to ribosomes. The antisense methods and protocols are generally described in, for example, C. Stein, A. Krieg, eds., "Applied Antisense Oligonucleotide Technology" Wiley-Liss, Inc. (1998); or U.S. Pat. Nos. 5,965,722; 6,339,066; 6,358,931; and 6,359,124.

The present invention also provides, as antisense molecules, nucleic acids or nucleotide sequences that contain a fragment, portion or variant that hybridizes under high stringency conditions to a nucleotide sequence of the GRP78 genes described herein, or their complementary strands. The nucleic acid fragments of the invention are at least about 12, generally at least about 15, 18, 21, or 25 nucleotides, and can be 40, 50, 70, 100, 200, or more nucleotides in length. Longer fragments, for example, 30 or more nucleotides in length, which encode antigenic polypeptides described hereinafter, are particularly useful, such as for the generation of antibodies.

Particular small nucleic acid molecules that are of use in the invention are short stretches of double stranded RNA that are known as short interfering RNAs (siRNAs). These interfering RNA (RNAi) allow for the selective inhibition of GRP78 gene function in vivo. In the present invention, siRNA has been used to knock-down GRP78 expression in an in vitro endothelial cell model of mucormycosis infection, and in doing so it demonstrates a dramatic effect on preventing endocytosis. The siRNA approach relies on an innate cellular response to combat viral infection. In this process, double stranded mRNAs are recognized and cleaved by the dicer RNase resulting in 21-23 nucleotide long stretches of RNAi. These RNAis are incorporated into and unwound by the RNA-inducing silencing complex (RISC). The single antisense strand then guides the RISC to mRNA containing the complementary sequence resulting in endonucleolytic cleavage of the mRNA, see Elbashir et al. (Nature 411; 494-498 (2001)). Hence, this technique provides a means for the targeting and degradation of GRP78 mRNA in vivo in a subject thus preventing the fungal pathogen.

The present invention further provides inhibitory antibodies (monoclonal or polyclonal) and antigen-binding fragments thereof, that are capable of binding to and inhibition of GRP78 polypeptide function. The antibody inhibitors of the present invention can bind to GRP78, or a portion, fragment, variant thereof, and interfere with or inhibit the protein function, i.e., receptor mediated penetration through and damage of endothelial cells by fungal pathogens. Furthermore, such antibodies can bind to GRP78 and interfere with or inhibit the proper localization or conformation of the protein within the host cell. An antibody, or antigen-binding fragment thereof, is said to "specifically bind," "immunologically bind," and/or is "immunologically reactive" to an GRP78 polypeptide of the invention if it reacts at a detectable level with the GRP78 polypeptide, and does not react detectably with unrelated polypeptides under similar conditions.

In addition, recombinant antibodies, such as chimeric and humanized antibodies, including both human and non-human portions, which can be made using standard recombinant DNA techniques, are within the scope of the invention. Also included within the term "antibody" are fragments, such as the Fab, F(ab'). The GRP78 specific monoclonal antibodies of the invention have specific binding activity to GRP78, or a functional fragment thereof, in pathogenic fungi responsible for mucormycosis.

Methods for raising polyclonal antibodies, for example, in a rabbit, goat, mouse or other mammal, are well known in the art (Harlow and Lane, eds., "Antibodies: A laboratory Manual," Cold Spring harbor Laboratory Press (1999); Harlow et al., *Using Antibodies: A Laboratory Manual*, Cold Spring harbor Laboratory Press (1999); C. Borrebaeck, ed., *Antibody Engineering: A Practical Guide*, W.H. Freeman and Co., Publishers, pp. 130-120 (1991)). The production of antipeptide antibodies commonly involves the use of host animals such as rabbits, mice, guinea pigs, or rats. If a large amount of serum is needed, larger animals such as sheep, goats, horses, pigs, or donkeys can be used. Animals are usually chosen based on the amount of antiserum required and suitable animals include rabbits, mice, rats, guinea pigs, and hamsters. These animals yield a maximum of 10-50 µL, 100-200 µL and 1-2 mL of serum per single bleed, respectively (Harlow and Lane, supra, 1999). Rabbits are very useful for the production of polyclonal antisera, since they can be safely and repeatedly bled and produce high volumes of antiserum. Two injections two to four weeks apart with 15-50 µg of antigen in a suitable adjuvant such as, for example, Freund's Complete Adjuvant can be followed by blood collection and analysis of the antiserum.

In addition, monoclonal antibodies can be obtained using methods that are well known and routine in the art (Harlow and Lane, supra, 1999). A peptide portion of a protein such as GRP78, for use as an immunogen, can be determined by methods well known in the art. Spleen cells from an immunized mouse can be fused to an appropriate myeloma cell line to produce hybridoma cells. Cloned hybridoma cell lines can be screened using a labeled protein to identify clones that secrete the corresponding antibodies, respectively. Hybridomas expressing the monoclonal antibodies having a desirable specificity and affinity can be isolated and utilized as a continuous source of the antibody.

Humanized antibodies can be constructed by conferring essentially any antigen binding specificity onto a human antibody framework. Methods of constructing humanized antibodies are useful to prepare an antibody appropriate for practicing the methods of the invention and avoiding host immune responses against the antibody when used therapeutically. The antibodies described herein can be used to generate therapeutic modulating substances for reducing the severity of a condition associated with fibroblast mediated.

Humanization of an antibody can be accomplished by methods well known in the art such as complementary determining region (CDR)-grafting and optimization of framework and CDR residues. For example, humanization of an antibody can be accomplished by CDR-grafting as described in Fiorentini et al., *Immunotechnology* 3(1): 45-59 (1997), which is incorporated herein be reference. Briefly, CDR-grafting involves recombinantly splicing CDRs from a nonhuman antibody into a human framework region to confer binding activity onto the resultant grafted antibody, or variable region binding fragment thereof. Once the CDR-grafted antibody, or variable region binding fragment is made, binding affinity comparable to the nonhuman antibody can be reacquired by subsequent rounds of affinity maturation strategies known in the art. Humanization of a rabbit polyclonal antibody can be accomplished by similar methods as described in Rader et al., *J. Biol. Chem.* 275(18): 13668-13676 (2000), which is incorporated herein be reference.

Humanization of a nonhuman antibody useful as a modulating substance for practicing a method of the invention can also be achieved by simultaneous optimization of framework and CDR residues, which permits the rapid identification of co-operatively interacting framework and CDR residues, as described in Wu et al., *J. Mol. Biol.* 294(1): 151-162 (1999), which is incorporated herein by reference. Briefly, a combinatorial library that examines a number of potentially important framework positions is expressed concomitantly with focused CDR libraries consisting of variants containing random single amino acid mutations in the third CDR of the heavy and light chains. By this method, multiple Fab variants containing as few as one nonhuman framework residue and displaying up to approximately 500-fold higher affinity than the initial chimeric Fab can be identified. Screening of combinatorial framework-CDR libraries permits identification of monoclonal antibodies with structures optimized for function, including instances in which the antigen induces conformational changes in the monoclonal antibody. The enhanced humanized variants contain fewer nonhuman framework residues than antibodies humanized by sequential in vitro humanization and affinity maturation strategies known in the art.

It is further contemplated that a modulating substance useful for practicing a method of the invention can be a human antibody. Human antibodies can be produced by methods known in the art that involve immunizing a transgenic non-human animal with the desired antigen. The transgenic non-human animal can be modified such that it fails to produce endogenous antibodies, but instead produces B-cells which secrete fully human immunoglobulins. The antibodies produced can be obtained from the animal directly or from immortalized B-cells derived from the transgenic nonhuman animal. Alternatively, the genes encoding the immunoglobulins with human variable regions can be recovered and expressed to obtain the antibodies directly or modified to obtain analogs of antibodies such as, for example, single chain $F_v$ molecules. Thus, it is contemplated to produce a modulating substance useful for practicing a method of the invention that is a fully human immunoglobulin to a specific antigen or to produce an analog of the immunoglobulin by a process that includes immunizing a nonhuman animal with antigen under conditions that stimulate an immune response.

The nonhuman animal that produces a human antibody can be modified to be substantially incapable of producing endogenous heavy or light immunoglobulin chain, but capable of producing immunoglobulins with both human variable and constant regions. In the resulting immune response, the animal produces B cells which secrete immunoglobulins that are fully human and specific for the antigen, for example, GRP78. The human immunoglobulin of desired specificity can be directly recovered from the animal, for example, from the serum, or primary B cells can be obtained from the animal and immortalized. The immortalized B cells can be used directly as the source of human antibodies or, alternatively, the genes encoding the antibodies can be prepared from the immortalized B cells or from primary B cells of the blood or lymphoid tissue, for example, spleen, tonsils, lymph nodes, bone marrow, of the immunized animal and expressed in recombinant hosts, with or without modifications, to produce the immunoglobulin or its analogs. In addition, the genes encoding the repertoire of immunoglobulins produced by the immunized animal can be used to generate a library of immunoglobulins to permit screening for those variable regions which provide the desired affinity. Clones from the library which have the desired characteristics can then be used as a source of nucleotide sequences encoding the desired variable regions for further manipulation to generate human antibodies or analogs with these characteristics using standard recombinant techniques. Various techniques for preparing human antibodies using transgenic nonhuman animals, for example, transgenic mice, are well known in the art and described, for example, in Fishwild et al., *Nature Biotechnology* 14: 845-851 (1996); Heijnen et al., *Journal of Clinical Investigation* 97: 331-338 (1996); Lonberg et al. *Nature* 368: 856-859 (1994); Morrison, *Nature* 368:812-813 (1994); Neuberger, *Nature Biotechnology* 14: 826 (1996); Chadd and Chamow, *Curr. Opin. Biotechnol.* 12(2):188-94 (2001); Russel et al., *Infection and Immunity* 1820-1826 (2000); Gallo et al., *European Journal of Immunology* 30:534-540 (2000); Davis et al., *Cancer Metastasis Rev.* 18(4):421-5 (1999); Green, *Journal of Immunological Methods* 231:11-23 (1999) Yang et al., *Journal of Leukocyte Biology* 66:401-410 (1999); Jakobovits, *Advanced Drug Delivery Reviews* 31:33-42 (1998); Green and Jakobovits, *J. Exp. Med.* 188(3):483-495 (1998); Jakobovits, *Exp. Opin. Invest. Drugs* 7(4):607-614 (1998); Mendez et al., *Nature Genetics* 15:146-156 (1997); Jakobovits, *Weir's Handbook of Experimental Immunology, The Integrated Immune System*, Vol. IV: 194.1-194.7 (1996), each of which is incorporated herein by reference. Furthermore, various techniques known in the art for preparation of a human antibody are described in U.S. Pat. Nos. 6,162,963; 6,150,584; 6,114,598; 6,111,166; 6,096,311 and 6,075,181, each of which is incorporated herein by reference.

As described herein, an antibody can be a modulating substance useful for practicing a method of the invention and can include, for example, a polyclonal antibody, monoclonal antibody as well as recombinant versions and functional fragments thereof. Recombinant versions of antibodies include a wide variety of constructions ranging from simple expression and co-assembly of encoding heavy and light chain cDNAs to speciality constructs termed designer antibodies. Recombinant methodologies, combined with the extensive characterization of polypeptides within the immunoglobulin superfamily, and particularly antibodies, provides the ability to design and construct a vast number of different types, styles and specificities of binding molecules derived from immunoglobulin variable and constant region binding domains. Specific examples include chimeric antibodies, where the constant region of one antibody is substituted with that of another antibody, and humanized antibodies, described above, where the complementarity determining regions (CDR) from one antibody are substituted with those from another antibody.

Other recombinant versions of antibodies include, for example, functional antibody variants where the variable region binding domain or functional fragments responsible for maintaining antigen binding is fused to an $F_C$ receptor binding domain from the antibody constant region. Such variants are essentially truncated forms of antibodies that remove regions non-essential for antigen and $F_C$ receptor binding. Truncated variants can have single valency, for example, or alternatively be constructed with multiple valencies depending on the application and need of the user. Additionally, linkers or spacers can be inserted between the antigen and $F_C$ receptor binding domains to optimize binding activity as well as contain additional functional domains fused or attached to effect biological functions other than, for example, binding to a receptor autoantigen so as to inhibit its interaction with an endogenous immunoglobulin; binding to a chemoattractant molecule or its receptor to neutralize the cell recruitment activity of the chemoattractant molecule; or binding to a chemoattractant molecule receptor to prevent the release of the chemottractant molecule from a fibroblast cell. Those skilled in the art will know how to construct recombinant antibodies in light of the art knowledge regarding antibody engineering and given the guidance and teachings herein. A description of recombinant antibodies, functional fragments and variants and antibody-like molecules can be found, for example, in "Antibody Engineering," 2nd Edition, (Carl A. K. Borrebaeck, Ed.) Oxford University Press, New York, (1995).

Additional functional variants of antibodies that can be used as modulating substances useful for practicing a method of the invention include antibody-like molecules other than antigen binding-$F_C$ receptor binding domain fusions. For example, antibodies, functional fragments and fusions thereof containing a $F_C$ receptor binding domain can be produced to be bispecific in that one variable region binding domain exhibits binding activity for one antigen and the other variable region binding domain exhibits binding activity for a second antigen. Such bispecific antibodies can be advantageous in the methods of the invention because a single bispecific antibody will contain two different target antigen binding species. Therefore, a single molecular entity can be administered to achieve neutralization of, for example, GRP78.

An antibody useful as a modulating substance for practicing the method of the invention can also be an immunoadhesion or bispecific immunoadhesion. Immunoadhesions are antibody-like molecules that combine the binding domain of a non-antibody polypeptide with the effector functions of an antibody of an antibody constant domain. The binding domain of the non-antibody polypeptide can be, for example, a ligand or a cell surface receptor having ligand binding activity. Immunoadhesions can contain at least the $F_C$ receptor binding effector functions of the antibody constant domain. Specific examples of ligands and cell surface receptors that can be used for the antigen binding domain of an immunoadhesion include, for example, a T cell receptor such as the CCR5 receptor that recognizes GRP78. It is understood that other ligands and ligand receptors known in the art can similarly be used for the antigen binding domain of an immunoadhesion. In addition, multivalent and multispecific immunoadhesions can be constructed for use as a modulating substance for reducing the severity of a condition associated with fibroblast mediated T-lymphocyte infiltration. The construction of bispecific antibodies, immunoadhesions, bispecific immunoadhesions and other heteromultimeric polypeptides which can be used in the invention methods is the individual matter of, for example, U.S. Pat. Nos. 5,807,706 and 5,428,130, which are incorporated herein by reference.

Moreover, portions or fragments or variants of the GRP78 nucleotide sequence identified herein (and the corresponding complete gene sequence) can be used in various ways as polynucleotide reagents. For example, these sequences can be used to identify and express recombinant polypeptides for analysis, characterization, or therapeutic use. The sequences can additionally be used as reagents in the screening and/or diagnostic assays described hereinafter, and can also be included as components of kits (e.g., diagnostic kits) for use in the screening and/or diagnostic assays.

The compositions of the present invention in inhibiting GRP78 can be applied to subjects who are suffering from a wide variety of fungal infections including zygomycosis and mucormycosis. The compositions of the invention can further be supplemented with other antifungal agents (e.g., Amphotericin, Deferiprone, Deferasirox). Alternatively, the compositions of the invention can be applied prophylactically to all subjects who are at high risk of developing mucormycosis or other fungal infections (e.g., via active immunization). This would not be considered an over treatment giving the high mortality and morbidity of mucormycosis in view of the current antifungal and surgical debridement treatment.

Further, the invention is also directed to host cells in which immunogenic GRP78 polypeptides or GRP78 inhibitory nucleotides (e.g., siRNA or antisense molecules) can be produced. The term "host cell" is understood to refer not only to the particular subject cell but also to the progeny or potential progeny of the foregoing cell. A host cell can be any prokaryotic (e.g., *E. coli*) or eukaryotic cell (e.g., yeast, insect cells, or mammalian cells, such as CHO or COS cells). Other suitable host cells are known to those skilled in the art. Vectors expressing such immunogenic inhibitory molecules can be introduced into prokaryotic or eukaryotic cells via conventional transfection or transformation techniques (see, Sambrook et al., *Molecular Cloning: A Laboratory Manual*, Cold Spring Harbor Laboratories, Cold Spring Harbor, N.Y., 1989).

According to another aspect of the present invention, any of the above-described compositions can be used for treating or prevention of a fungal condition. A fungal condition is an aberrant condition or infection causes by a pathogenic fungus. Symptoms of a fungal condition that can be ameliorated by a method of the invention include, for example, fever, chills, night sweats, anorexia, weight loss, malaise, depression and lung, skin or other lesions. Other symptoms or characteristic manifestations include, for example, dissemination from a primary focus, acute or subacute presentations, progressive pneumonia, fungemia, manifestations of extrapulmonary dissemination, chronic meningitis, progressive disseminated histoplasmosis as a generalized involvement of the reticuloendothelial system (liver, spleen, bone marrow) and blastomycosis as single or multiple skin lesions. Effective treatment of an individual with a fungal condition, for example, will result in a reduction one or more of such symptoms in the treated individual. Numerous other clinical symptoms of fungal conditions are well known in the art and also can be used as a measure of amelioration or reduction in the severity of a fungal condition using the methods of the invention described herein.

Diagnosis of a fungal condition can be confirmed by isolating causative fungi from, for example, sputum, urine, blood, bone marrow, or specimens from infected tissues. For example, fungal infections can be diagnosed histopathologically with a high degree of reliability based on distinctive morphologic characteristics of invading fungi and/or by immunohistochemistry and the like selective for identifying antigens. Assessment of the activity of the infection also can be based on cultures taken from many different sites, fever, leukocyte counts, clinical and laboratory parameters related to specific involved organs (eg, liver function tests), and immunoserologic tests. The clinical significance of positive sputum cultures also can be corroborated by confirmation of tissue invasion.

Fungal infection, or mycoses, of humans and animals include, for example, superficial fungal infections that affect the outer layers of skin; fungal infections of the mucous membranes including the mouth (thrush), vaginal and anal regions, such as those caused by *Candida albicans*, and fungal infections that affect the deeper layers of skin and internal organs are capable of causing serious, often fatal illness, such as those caused by, for example, *Rhizopus oryzae*. Fungal infections are well known in the art and include, for example, zygomycosis, mucormycosis, aspergillosis, cryptococcosis, candidiasis, histoplasmosis, coccidiomycosis, paracoccidiomycosis, fusariosis (hyalohyphomycoses), blastomycosis, penicilliosis or sporotrichosis. These and other fungal infections can be found described in, for example, Merck Manual, Sixteenth Edition, 1992, and in Spellberg et al., *Clin. Microbio. Rev.* 18:556-69 (2005).

The fungal conditions caused by fungi of the genus *Candida*, candidiasis, can occur, for example, in the skin and mucous membranes of the mouth, respiratory tract and/or vagina as well as invade the bloodstream, especially in immunocompromised individuals. Candidiasis also is known in the art as candidosis or moniliasis. Exemplary species of the genus *Candida* include, for example, *Candida albicans*, *Candida krusei*, *Candida tropicalis*, *Candida glabrata* and *Candida parapsilosis*.

The fungal diseases caused by the genus *Aspergillus* include, for example, allergic aspergillosis, which affects asthma, cystic fibrosis and sinusitis patients; acute invasive aspergillosis, which shows increased incidence in patients with weakened immunity such as in cancer patients, patients undergoing chemotherapy and AIDS patients; disseminated invasive aspergillosis, which is widespread throughout the body, and opportunistic *Aspergillus* infection, which is characterized by inflammation and lesions of the ear and other organs. *Aspergillus* is a genus of around 200 fungi. *Aspergillus* species causing invasive disease include, for example, *Aspergillus fumigatus* and *Aspergillus flavus*. *Aspergillus* species causing allergic disease include, for example, *Aspergillus fumigatus* and *Aspergillus clavatus*. Other exemplary *Aspergillus* infectious species include, for example, *Aspergillus terreus* and *Aspergillus nidulans*.

The fungal conditions such as, for example, zygomycosis and mucormycosis which are caused by saprophytic mould fungi include rhinocerebral mucormycosis, pulmonary mucormycosis, gastrointestinal mucormycosis, disseminated mucormycosis, bone mucormycosis, mediastinum mucormycosis, trachea mucormycosis, kidney mucormycosis, peritoneum mucormycosis, superior vena cava mucormycosis or external otitis mucormycosis. Infectious agents causing mucormycosis are of the order Mucorales which include species from *Rhizopus* genus such as, for example, *Rhizopus oryzae* (*Rhizopus arrhizus*), *Rhizopus microsporus*, *Rhizopus microsporus* var. *rhizopodiformis*; or species from *Absidia* genus such as, for example, *Absidia corymbifera*; or species from *Apophysomyces* genus such as, for example, *Apophysomyces elegans*; or species from *Mucor* genus such as, for example, *Mucor amphibiorum*; or species from *Rhizomucor* genus such as, for example, *Rhizomucor pusillus*; or species from *Cunninghamell* genus (in the Cunninghamellaceae family) such as, for example, *Cunninghamella bertholletiae*.

Various methods are described herein for effective inhibition of GRP78 molecule and/or its function in treatment of mucormycosis and other fungal diseases. These inhibiting methods involve vaccines, antisense, siRNA, antibody, or any other compositions capable of effectively targeting and inhibiting the function of GRP78. Such methods will reduce or prevent the growth of the fungus in the infected tissues by inhibiting the penetration through and damage of endothelial cells. An immunotherapeutic inhibition of fungal penetration through and damage of endothelial cells using a GRP78 antibody, polypeptide or functional fragment thereof or a variant thereof is useful in this context because: (i) the morbidity and mortality associated with mucormycosis, for example, continues to increase, even with currently available antifungal therapy; (ii) a rising incidence of antifungal resistance is associated with the increasing use of antifungal agents; iii) the population of patients at risk for serious zygomycosis, mucormycosis, candidosis, or aspergillosis, for example, is well-defined and very large, and includes, e.g., post-operative patients, transplant patients, cancer patients, low birth weight infants, subjects with diabetes ketoacidosis (DKA) and other forms of metabolic acidosis, subjects receiving treatment with corticosteroids, subjects with neutropenia, trauma, burns, and malignant hematological disorders, and subjects receiving deferoxamine chelation-therapy or hemodialysis; and iv) a high percentage of the patients who develop serious fungal infections are not neutropenic, and thus can respond to a vaccine or a competitive polypeptide or compound inhibitor. For these reasons, Zygomycetes or *Candida*, for example, are fungal targets for passive immunotherapy, active immunotherapy or a combination of passive or active immunotherapy.

Without be bound by theory, it is completed that mechanistically, GRP78 polypeptide acts in a receptor dependent manor for pathogenic fungal penetration and damage of endothelial cells. More specifically, the germling form of the fungus binds to the GRP78 membrane bound polypeptide and the GRP79 polypeptide mediated germling endocytosis by endothelial cells but not adherence to the endothelial cells.

Therefore, the methods of the present invention in inhibiting GRP78 can be applied to subjects who are suffering from a wide variety of fungal infections including zygomycosis and mucormycosis. The methods of the invention can further be supplemented with other antifungal agents (e.g., Amphotericin, Deferiprone, Deferasirox). Alternatively, the methods of the invention can be applied prophylactically to all subjects who are at high risk of developing mucormycosis or other fungal infections (e.g., via active immunization). This would not be considered an over treatment giving the high mortality and morbidity of mucormycosis in view of the current antifungal and surgical debridement treatment.

Accordingly, in one aspect, the invention provides a method of treating or preventing disseminated mucormycosis or other fungal conditions. The method includes administering to a subject having, or susceptible to having, a fungal condition an immunogenic amount of a GRP78 polypeptide, or an immunogenic fragment thereof in a pharmaceutically acceptable medium or adjuvant. The preparation of vaccines is generally described in, for example, M. F. Powell and M. J. Newman, eds., "Vaccine Design (the subunit and adjuvant approach)," Plenum Press (1995); A. Robinson, M. Cranage, and M. Hudson, eds., "Vaccine Protocols (Methods in Molecular Medicine)," Humana Press (2003); and D. Ohagan, ed., "Vaccine Adjuvants: Preparation Methods and Research Protocols (Methods in Molecular Medicine)," Humana Press (2000).

The vaccine compositions are administrated in a manner compatible with the dosage formulation and in such amount as will be prophylactically effective with or without an adjuvant. The quantity to be administered, which is generally in the range of 1 to 10 mg, preferably 1 to 1000 µg of antigen per dose, depends on the subject to be treated, capacity of the subject's immune system to synthesize antibodies, and the degree of protection desired. Precise amounts of active ingredient required to be administered can depend on the judgment of the practitioner and can be peculiar to each subject. Moreover, the amount of polypeptide in each vaccine dose is selected as an immunogenic amount which induces an immunoprotective response. Particularly useful immunogenic amounts include an amount of GRP78 polypeptide that also is devoid of significant, adverse side effects. Such amount will vary depending upon the immunogenic strength of an GRP78 polypeptide selected for vaccination. Useful immunogenic amounts of an GRP78 polypeptide or immunogenic fragment thereof include, for example, doses ranging from about 1-1000 µg. In certain embodiments, useful immunogenic amounts of an GRP78 polypeptide or immunogenic fragment thereof include about 2-100 µg, and particularly useful dose ranges can range from about 4-40 µg, including for example, 5, 6, 7, 8, 9, 10, 12, 15, 20, 25, 30, 35 and 40 µg as well as all values in between the above exemplified amounts. An optimal immunogenic amount for a selected GRP78 polypeptide vaccine of the invention can be ascertained using methods well known in the art such as determination of antibody titres and other immune responses in subjects as exemplified previously. Following an initial vaccination, subjects receive a boost in about 3-4 weeks. Vaccine delivery methods is further described, for example, in S. Cohen and H. Bernstein, eds., "Microparticulate Systems for the Delivery of Proteins and Vaccines (Drugs and The Pharmaceutical Sciences)," Vol. 77, Marcel Dekker, Inc. (1996). Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

In another embodiment, the invention provides a method for treating or preventing a fungal condition, comprising administering to a subject having, or susceptible to having, a fungal condition a therapeutically effective amount of an antisense RNA selected from the group consisting of a nucleotide sequence that is substantially complimentary to a portion of an GRP78 nucleic acid sequence or a nucleotide sequence that is substantially complimentary to at least 12 contiguous nucleotide bases of GRP78 sequence and a pharmaceutically acceptable excipient or carrier.

The antisense oligonucleotides used in accordance with this invention can be conveniently and routinely made through the well-known technique of solid phase synthesis. Equipment for such synthesis is sold by several vendors including Applied Biosystems. Any other means for such synthesis can also be employed, however the actual synthesis of the oligonucleotides are well within the talents of those skilled in the art. It is also well known to use similar techniques to prepare other oligonucleotides such as the phosphorothioates and alkylated derivatives. As described earlier, an antisense nucleic acid molecule (e.g., an antisense oligonucleotide) can be chemically synthesized using naturally occurring nucleotides or variously modified nucleotides designed to hybridize with a control region of a gene (e.g., promoter, enhancer, or transcription initiation region) to inhibit the expression of the GRP78 gene through triple-helix formation. Alternatively, the antisense nucleic acid molecule can be designed to hybridize with the transcript of GRP78 (i.e., mRNA), and thus inhibit the translation of GRP78 by inhibiting the binding of the transcript to ribosomes. The antisense methods and protocols are generally described in, for example, C. Stein, A. Krieg, eds., "Applied Antisense Oligonucleotide Technology" Wiley-Liss, Inc. (1998); or U.S. Pat. Nos. 5,965,722; 6,339,066; 6,358,931; and 6,359,124.

The antisense compositions of the invention can be delivered to a subject in need thereof with variety of means known in the art. For example, microparticles such as polystyrene microparticles, biodegradable particles, liposomes or microbubbles containing the antisense compositions in releasable form can be used for direct delivery of the compositions into tissues via injection. In some embodiments of the invention, the antisense oligonucleotides can be prepared and delivered in a viral vector such as hepatitis B virus (see, for example, Ji et al., J. Viral Hepat. 4:167 173 (1997)); in adeno-associated virus (see, for example, Xiao et al. Brain Res. 756:76 83 (1997)); or in other systems including but not limited to an HVJ (Sendai virus)-liposome gene delivery system (see, for example, Kaneda et al. Ann. N.Y. Acad. Sci. 811:299 308 (1997)); a "peptide vector" (see, for example, Vidal et al. CR Acad. Sci III 32):279 287 (1997)); as a gene in an episomal or plasmid vector (see, for example, Cooper et al. Proc. Natl. Acad. Sci. U.S.A. 94:6450 6455 (1997), Yew et al. Hum Gene Ther. 8:575 584 (1997)); as a gene in a peptide-DNA aggregate (see, for example, Niidome et al. J. Biol. Chem. 272:15307 15312 (1997)); as "naked DNA" (see, for example, U.S. Pat. No. 5,580,859 and U.S. Pat. No. 5,589,466); in lipidic vector systems (see, for example, Lee et al. Crit Rev Ther Drug Carrier Syst. 14:173 206 (1997)); polymer coated liposomes (Marin et al., U.S. Pat. No. 5,213,804 issued Can 25, 1993; Woodle et al., U.S. Pat. No. 5,013,556 issued Can 7, 1991); cationic liposomes (Epand et al., U.S. Pat. No. 5,283,185 issued Feb. 1, 1994; Jessee, J. A. U.S. Pat. No. 5,578,475 issued Nov. 26, 1996; Rose et al, U.S. Pat. No. 5,279,833 issued Jan. 18, 1994; Gebeyehu et al., U.S. Pat. No. 5,334,761 issued Aug. 2, 1994); gas filled microspheres (Unger et al., U.S. Pat. No. 5,542,935 issued Aug. 6, 1996), ligand-targeted encapsulated macromolecules (Low et al. U.S. Pat. No. 5,108,921 issued Apr. 28, 1992; Curiel et al., U.S. Pat. No. 5,521,291 issued Can 28, 1996; Groman et al., U.S. Pat. No. 5,554,386 issued Sep. 10, 1996; Wu et al., U.S. Pat. No. 5,166,320 issued Nov. 24, 1992).

The invention also provides a method of treating or preventing a fungal condition in a subject in need thereof, including exposing said fungi to a small interfering RNA against GRP78. In one aspect, small interfering RNA sequence that is substantially complimentary to at least 18 contiguous nucleotide bases of GRP78 sequence is used that is capable of binding to an GRP78 nucleotide sequence or a fragment thereof. In another aspect the small interfering RNA includes the nucleotide sequence CTTGTTGGTGGCTCGACTCGA (SEQ ID NO. 1).

Double-stranded RNA (dsRNA) also known as small-interfering RNA (siRNA) induces sequence-specific post-transcriptional gene silencing in many organisms by a process known as RNA interference (RNAi). In the present invention, as described in Example I, RNAi has been prepared and used to knock-down GRP78 expression in a DKA mouse model of mucormycosis infection, and in doing so it demonstrates a dramatic effect on survival and protection against the infection.

The siRNA is usually administered as a pharmaceutical composition. The administration can be carried out by known methods, wherein a nucleic acid is introduced into a desired target cell in vitro or in vivo. Commonly used gene transfer techniques include calcium phosphate, DEAE-dextran, electroporation and microinjection and viral methods (Graham et al. Virol. 52, 456 (1973); McCutchan et al. J. Natl. Cancer Inst. 41, 351(1968); Chu et al. Nucl. Acids Res. 15, 1311 (1987); Fraley et al. J. Biol. Chem. 255, 10431 (1980); Capecchi, Cell 22, 479 (1980); and cationic liposomes (Feigner et al. Proc. Natl. Acad. Sci USA 84, 7413 (1987)). Commercially available cationic lipid formulations are e.g. Tfx 50™ (Promega) or Lipofectamin2000™ (Invitrogen).

The invention also provides a method of treating or preventing a fungal condition in a subject in need thereof, including administering a therapeutically effective amount of an antibody inhibitor of GRP78. In one embodiment, the antibody inhibitor of GRP78 is an antibody or antibody fragment that specifically binds to an GRP78 nucleotide polypeptide or a fragment thereof.

As described earlier the antibody inhibitors of GRP78 are capable of binding to and inhibition of GRP78 function. The antibody inhibitors of the present invention can bind to GRP78, a portion, fragment, or variant thereof, and interfere with or inhibit the protein function. These antibodies can inhibit GRP78 by negatively affecting, for example, the protein's proper membrane localization, folding or conformation, its substrate binding ability.

The antibodies of the present invention can be generated by any suitable method known in the art. Polyclonal antibodies against GRP78 can be produced by various procedures well known in the art. For example, an GRP78 peptide antigenic can be administered to various host animals including, but not limited to, rabbits, mice, rats, etc. to induce the production of sera containing polyclonal antibodies specific for the antigen. Various adjuvants can be used to increase the immunological response, depending on the host species, and include but are not limited to, Freund's (complete and incomplete), mineral gels such as aluminum hydroxide, alum (ALHYDROGEL), surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

GRP78 peptide antigens suitable for producing antibodies of the invention can be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)). Monoclonal antibodies of the present invention can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties).

The antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

The antibodies of the invention can be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art. See, e.g., Sambrook, Fitsch & Maniatis, *Molecular Cloning: A Laboratory Manual*, Second Edition Cold Spring Harbor Laboratory Press, Cold Spring Harbor, N.Y. (1989).

Specific binding can be determined by any of a variety of measurements known to those skilled in the art including, for example, affinity ($K_a$ or $K_d$), association rate ($k_{on}$), dissociation rate ($k_{off}$), avidity or a combination thereof. Antibodies of the present invention can also be described or specified in terms of their binding affinity to GRP78. Preferred binding affinities include those with a dissociation constant or $K_d$ less than $5\times10^{-2}$ M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$ M, $10^7$ M, $5\times10^{-8}$M, $10^{-8}$M, $5\times10^{-9}$M, $10^{-9}$M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

An exemplary approach in which the antibodies of the present invention can be used as GRP78 inhibitors includes binding to and inhibiting GRP78 polypeptides locally or systemically in the body or by direct cytotoxicity of the antibody, e.g. as mediated by complement (CDC) or by effector cells (ADCC). The antibodies of this invention can be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention can be administered alone or in combination with other types of treatments such as, for example, anti-fungal therapies. In one embodiment, GRP78 antibodies are administered to a human patient for therapy or prophylaxis.

Various delivery systems are known and can be used to administer the antibody inhibitors of the invention, e.g., encapsulation in liposomes, microparticles, microcapsules, recombinant cells capable Methods of introduction include but are not limited to intradermal, intramuscular, intraperitoneal, intravenous, subcutaneous, intranasal, epidural, and oral routes. The compounds or compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. Pulmonary administration can also be employed, e.g., by use of an inhaler or nebulizer, and formulation with an aerosolizing agent.

For antibodies, the dosage administered to a subject is typically 0.1 mg/kg to 100 mg/kg of the subject's body weight. Preferably, the dosage administered to a subject is between 0.1 mg/kg and 20 mg/kg of the subject's body weight, more preferably 1 mg/kg to 10 mg/kg of the subject's body weight. Generally, humanized or human antibodies have a longer half-life within the human body than antibodies from other species due to the immune response to the foreign polypeptides. Thus, lower dosages of humanized antibodies and less frequent administration is often possible. Further, the dosage and frequency of administration of antibodies of the invention can be reduced by enhancing uptake and tissue penetration (e.g., into the brain) of the antibodies by modifications such as, for example, lipidation.

In pharmaceutical dosage forms, the compositions of the invention including vaccine, antisense, siRNA and antibodies can be used alone or in appropriate association, as well as in combination, with each other or with other pharmaceutically active compounds. Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid or gaseous forms, such as tablets, capsules, powders, granules, ointments, solutions, suppositories, enemas, injections, inhalants and aerosols. The following methods and excipients are merely exemplary and are in no way limiting.

Any of treatment modalities disclosed herein can be combined and administered to a subject suffering from a fungal infection or being at risk for developing a fungal infection (prophylactic vaccination or treatment). In a combination therapy, for example, a subject can first receive a vaccine of the invention to generate an immune response towards the fungi, then an antisense, siRNA and/or antibody that can target GRP78 of the subject and further augment the fungal treatment. In one embodiment of the treatment, the vaccine of the invention is used in combination with an antisense, siRNA and/or antibody against GRP78 for treating or preventing a fungal condition such as, for example, mucormycosis. In another embodiment, the antibodies of the invention are used in combination with antisense and/or siRNA for treating the fungal condition.

The compositions of the inventions, either alone or in combination, can further be combined one or more methods or compositions available for fungal therapy. In one embodiment, the compositions of the invention can be used in concert with a surgical method to treat a fungal infection. In yet another embodiment, the compositions of the invention can be used in combination with a drug or radiation therapy for treating a fungal condition. Antifungal drugs that are useful for combination therapy with the compositions of the invention include, but are not limited to, amphotericin B, iron chelators such as, for example, deferasirox, deferiprone, POSACONAZOLE®, FLUCONAZOLE®, ITRACONAZOLE® and/or KETOCONAZOLE®. Radiations useful in combination therapies for treating fungal infections include electromagnetic radiations such as, for example, near infrared radiation with specific wavelength and energy useful for treating fungal infections. In combination therapy, chemotherapy or irradiation is typically followed by administration of the vaccine in such a way that the formation of an effective anti-fungal immune response is not compromised by potential residual effects of the prior treatment.

In a further embodiment of combination therapy, the compositions of the invention can be combined with immunocytokine treatments. Without wishing to be bound by theory, it is believed that, for example, a vaccine generates a more effective immune response against, for example, an infection when a cytokine promoting the immune response is present at the site of the infection. For example, useful immunocytokines are those that elicit Th1 response, such as IL-2 or IL-12. During a combination therapy, for example, a subject can first receive a vaccine of the invention to generate an immune response towards a fungal infection, then an immunocytokine that can target the fungi and support the immune response in fighting the infection. Preferred immunocytokines typically have, for example, an antibody moiety that recognizes a surface antigen characteristic of the fungi. Immunocytokines typically also have a cytokine moiety such as IL-2, IL-12, or others that preferentially direct a Th1 response. Immunocytokines suitable for the invention are described in U.S. Pat. No. 5,650,150, the contents of which are hereby incorporated by reference.

In another embodiment of combination therapy, combinations of the compositions of the invention can be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second. In another specific embodiment, compositions of the invention are used in any combination with amphotericin B, deferasirox, deferiprone, POSACONAZOLE®, FLUCONAZOLE®, ITRACONAZOLE®, and/or KETOCONAZOLE® to prophylactically treat, prevent, and/or diagnose an opportunistic fungal infection.

The invention, therefore, provides methods of treatment, inhibition and prophylaxis by administration to a subject of a therapeutically effective amount of one or more compounds or pharmaceutical compositions of the invention. In a preferred aspect, the compositions of the invention are substantially purified (e.g., substantially free from substances that limit their effect or produce undesired side-effects). The subject is preferably an animal, including but not limited to animals such as cows, pigs, horses, chickens, cats, dogs, etc., and is preferably a mammal, and most preferably human.

As discussed above, various delivery systems are known and can be used to administer the compositions of the invention. The compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local.

In a specific embodiment, it can be desirable to administer the pharmaceutical compounds or compositions of the invention locally to the area in need of treatment; this can be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including a vaccine or antibody, of the invention, care must be taken to use materials to which the protein does not absorb. In another embodiment, the compound or composition can be delivered in liposomes. In yet another embodiment, the compounds or compositions can be delivered in a controlled release system.

In an embodiment, the compositions are formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule indicating the quantity of active agent. Where the compositions are to be administered by infusion, they can be dispensed with an infusion bottle containing sterile pharmaceutical grade water or saline. Where the compositions are administered by injection, an ampoule of sterile water for injection or saline can be provided so that the ingredients can be mixed prior to administration.

The compounds of the invention can also be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compounds or compositions of the invention which will be effective in the treatment, inhibition and prevention of a fungal disease or condition can be determined by standard clinical techniques. In addition, in vitro assays can optionally be employed to help identify optimal dosage ranges. The precise dose to be employed in the formulation will also depend on the route of administration, and the seriousness of the disease or condition, and should be decided according to the judgment of the practitioner and each subject's circumstances. Effective doses can be extrapolated from dose-response curves derived from in vitro or animal model test systems.

It is understood that modifications which do not substantially affect the activity of the various embodiments of this invention are also included within the definition of the invention provided herein. Accordingly, the following examples are intended to illustrate but not limit the present invention.

Example I

Endothelial Cell Receptor GRP78 is Required for Mucormycosis Pathogenesis

Mucormycosis is a life-threatening infection caused by fungi of the order Mucorales, the most common etiologic species of which is *Rhizopus oryzae*. The most common predisposing risk factor for mucormycosis is diabetes mellitus, and it has been long established that patients with diabetic ketoacidosis (DKA) have a unique predisposition to this infection (Ibrahim et al., *Clinical Mycology*, Dismukes et al., eds. New York, N.Y.: Oxford University Press, pp. 241-251 (2003) Spellberg et al., *Clin Microbiol Rev.* 18(3):556-569 (2005)). Unfortunately, despite surgical debridement and first-line antifungal therapy, the overall mortality of mucormycosis remains unacceptably high, and survivors are typically left with considerable disfigurement from the infection and surgery (Spellberg (2005) supra,; Gleissner et al., *Leuk Lymphoma* 45(7):1351-1360 (2004)).

A hallmark of mucormycosis is the presence of extensive angioinvasion with resultant vessel thrombosis and tissue necrosis (Ibrahim et al., *Clinical Mycology*, Dismukes et al., eds. New York, N.Y.: Oxford University Press, pp. 241-251 (2003); Spellberg et al., (2005) supra). Ischemic necrosis of infected tissues can prevent delivery of leukocytes and antifungal agents to the foci of infection. Thus, angioinvasion is a key factor in the pathogenesis of mucormycosis. During angioinvasion, the organism invades and damages vascular endothelial cells. Therefore, understanding the mechanisms by which these processes occur will lead to new approaches to prevent and/or treat mucormycosis.

*R. oryzae* strains were previously described to adhere to human umbilical vein endothelial cells in vitro and invade these cells by induced endocytosis (Ibrahim et al., *Infect Immun.* 73(2):778-783 (2005)). Endocytosed *R. oryzae* damages endothelial cells, and prevention of endocytosis abrogates the ability of the organisms to cause endothelial cell damage (Ibrahim et al., (2005) supra). In the experiments described herein, the receptor responsible for *R. oryzae* adherence to and invasion through endothelial cells is described. Furthermore, the influence of glucose and iron levels to regulate the expression the receptor are shown to be consistent with those seen during DKA.

*R. oryzae* and Culture Conditions.

Several clinical Mucorales isolates were used in this study. *R. oryzae* 99-880 and *Mucor* sp 99-932 are brain isolates, while *R. oryzae* 99-892 and *Rhizopus* sp 99-1150 were isolated from lungs of infected patients and obtained from the Fungus Testing Laboratory, University of Texas Health Science Center at San Antonio, San Antonio, Tex., USA. *Cunninghamella bertholletiae* 182 is also a clinical isolate and was a gift from Thomas Walsh (NIH, Bethesda, Md., USA). *Rhizopus microsporus* ATCC 20577 is an environmental isolate obtained from ATCC. *A. fumigatus* AF293 and *C. albicans* SC5314 are clinical isolates that were used to determine whether anti-GRP78 Ab blocks endothelial cell damage caused by these two organisms. Mucorales were grown on potato dextrose agar (PDA; BD Biosciences—Diagnostic Systems) plates for 3-5 days at 37° C., while *A. fumigatus* and

*C. albicans* were grown on Sabouraud dextrose agar (SDA) plates for 2 weeks and 48 hours, respectively, at 37° C. The sporangiospores were collected in endotoxin-free Dulbecco's PBS containing 0.01% TWEEN 80 (for Mucorales) and 0.2% TWEEN 80 (for *A. fumigatus*), washed with PBS, and counted with a hemocytometer to prepare the final inocula. For *C. albicans*, blastospores were collected in PBS after the organisms were grown in YPD medium (1% yeast extract [Difco Laboratories], 2% Bacto Peptone [Difco Laboratories], and 2% glucose [Sigma-Aldrich]) at 30° C. overnight. To form germlings, spores were incubated in liquid YPD medium at 37° C. with shaking for 1-3 hours based on the assay under study. Germlings were washed twice with RPMI 1640 without glutamine (Irvine Scientific) for all assays used, except in experiments involving isolation of the endothelial cell receptor, for which the germlings were washed twice with PBS (plus $Ca^{2+}$ and $Mg^{2+}$).

Endothelial Cells and CHO Cells.

Endothelial cells were collected from umbilical vein endothelial cells by the method of Jaffe et al. (Jaffe et al., *J Clin Invest.* 52(11):2745-2756 (1973)). The cells were harvested by using collagenase and were grown in M-199 (Gibco BRL) enriched with 10% fetal bovine serum, 10% defined bovine calf serum, 1-glutamine, penicillin, and streptomycin (all from Gemini Bio-Products). Second-passage cells were grown to confluency in 96-well tissue culture plates (Costar) on fibronectin (BD Biosciences). All incubations were in 5% $CO_2$ at 37° C. The reagents were tested for endotoxin using a chromogenic limulus amebocyte lysate assay (BioWhittaker Inc.), and the endotoxin concentrations were less than 0.01 IU/ml. Endothelial cell collection was approved by the Institutional Review Board of Los Angeles Biomedical Research Institute at Harbor-UCLA Medical Center. CHO cell line C.1, which was derived from parental DHFRdeficient CHO cells engineered to overexpress GRP78s, was a gift of Randall Kaufman, University of Michigan, Ann Arbor, Mich., USA (Reddy et al., *J Biol Chem.* 278(23):20915-20924 (2003); Morris et al., *J Biol Chem.* 272(7):4327-4334 (1997)).

Extraction of Endothelial Cell Membrane Proteins.

Endothelial cell membrane proteins were extracted according to the method of Isberg and Leong (Isberg and Leong, *Cell* 60(5):861-871 (1990)). Briefly, confluent endothelial cells in 100-mm-diameter tissue culture dishes were rinsed twice with warm Dulbecco's PBS containing $Ca^{2+}$ and $Mg^{2+}$ (PBS-CM) and then incubated with EZ-Link Sulfo-NHS-LS-Biotin (0.5 mg/ml; Pierce) in PBS-CM for 12 minutes at 37° C. in 5% $CO_2$. The cells were then rinsed extensively with cold PBS-CM and scraped from the tissue culture dishes. The endothelial cells were collected by centrifugation at 500 g for 5 minutes at 4° C. and then lysed by incubation for 20 minutes on ice in PBS-CM containing 5.8% n-octyl-β-d-glucopyranoside (w/v) (Calbiochem) and protease inhibitors (1 mM phenylmethylsulfonyl fluoride, 1 μg/ml pepstatin A, 1 μg/ml leupeptin, and 1 μg/ml aprotinin) (Sigma-Aldrich). The cell debris was removed by centrifugation at 5,000 g for 5 minutes at 4° C. The supernatant was collected and centrifuged at 100,000 g for 1 hour at 4° C. The concentration of the endothelial cell proteins in the resulting supernatant was determined using the Bradford method (Bio-Rad).

Isolation of Endothelial Cell Receptors that Bind to Mucorales.

Live Mucorales spores ($8 \times 10^8$) or an equivalent volume of 1-3 hour germlings (approximately $2 \times 10^8$ cells) were incubated for 1 hour on ice with 250 μg of biotin-labeled endothelial cell surface proteins in PBS-CM plus 1.5% n-octyl-β-d-glucopyranoside and protease inhibitors. The unbound endothelial cell proteins were washed away by 3 rinses with this buffer. The endothelial cell proteins that remained bound to the fungal cells were eluted twice with 6 M urea (Fluka), and the supernatant was combined and concentrated to an appropriate volume with a Microcon centrifugal filter (10,000 MWCO; Millipore). The proteins were then separated on 10% SDS-PAGE and transferred to PVDF-plus membranes (GE Water & Process Technologies). The membrane was then treated with Western Blocking Reagent (Roche) and probed with a mouse anti-biotin monoclonal Ab (Sigma-Aldrich). The membrane was then washed and incubated with secondary Ab, HRP-conjugated sheep anti-mouse IgG (Sigma-Aldrich). After incubation with SuperSignal West Dura Extended Duration Substrate (Pierce), the signals were detected using a CCD camera.

To identify endothelial cell proteins that bound to Mucorales, endothelial cell membrane proteins were incubated with *R. oryzae* germlings as above. The eluted proteins were separated by SDS-PAGE, and the gel was stained with SYPRO Ruby (Molecular Probes, Invitrogen). The major band at approximately 75 kDa was excised and microsequenced using MALDITOF MS/MS (Emory University Microchemical Facility).

To confirm the identity of GRP78, endothelial cell membrane proteins that bound to *R. oryzae* were separated on an SDS-polyacrylamide gel and transferred to PVDF-plus membranes. Membranes were probed with a rabbit anti-GRP78 Ab (Abcam), followed by HRP-conjugated goat anti-rabbit IgG (Pierce) as a secondary Ab. After incubation with SuperSignal West Dura Extended Duration Substrate (Pierce), the signals were detected using a CCD camera.

Colocalization of GRP78 with Phagocytosed *R. oryzae* Germlings by Indirect Immunofluorescence.

A modified method as previously described was used (Phan et al., *J Biol Chem.* 280(11):10455-10461 (2005)). Confluent endothelial cells on a 12-mm-diameter glass coverslip were infected with $10^5$/ml *R. oryzae* cells in RPMI 1640 medium that had been pregerminated for 1 or 3 hours. After 60 minutes incubation at 37° C., the cells were gently washed twice with HBSS to remove unbound organisms and then fixed with 3% paraformaldehyde. After washing with 1% BSA (Fisher) prepared in PBS-CM, the cells were incubated for 1 hour with rabbit anti-GRP78 Ab (Abcam), then counterstained with ALEXA FLUOR 488-labeled goat anti-rabbit IgG (Molecular Probes, Invitrogen). Cells were then permeabilized for 5 minutes in 0.5% TRITON X-100 and incubated with ALEXA FLUOR 568-labeled phalloidin (Molecular Probes) for 1 hour to detect F-actin. After washing, the coverslip was mounted on a glass slide with a drop of ProLong Gold antifade reagent (Molecular Probes, Invitrogen) and viewed by confocal microscopy. The final confocal images were produced by combining optical sections taken through the z axis.

Interactions of Fungi with Endothelial or CHO Cells.

The number of organisms endocytosed by endothelial cells or CHO cells was determined using a modification of a previously described differential fluorescence assay (Ibrahim et al., *Infect Immun.* 63(11):4368-4374 (1995)). Briefly, 12-mm glass coverslips in a 24-well cell culture plate were coated with fibronectin for at least 4 hours and seeded with endothelial or CHO cells until confluency. After washing twice with prewarmed HBSS, the cells were then infected with $10^5$ cells of *R. oryzae* in RPMI 1640 medium that had been germinated for 1 hour. Following incubation for 3 hours, the cells were fixed in 3% paraformaldehyde and were stained for 1 hour with 1% Uvitex (a gift from Jay Isharani, Ciba-Geigy, Greensboro, N.C., USA), which specifically binds to the chitin of the fungal cell wall. After washing 3 times with PBS, the coverslips were mounted on a glass slide with a drop of ProLong Gold antifade reagent and sealed with nail polish. The total number of cell-associated organisms (i.e., germlings adhering to monolayer) was determined by phase-contrast microscopy. The same field was examined by epifluorescence microscopy, and the number of uninternalized germlings (which were brightly fluorescent) was determined. The number of endocytosed organisms was calculated by subtracting the number of fluorescent organisms from the total number of visible organisms. At least 400 organisms were counted in 20-40 different fields on each slide. Two slides per arm were used for each experiment, and the experiment was performed in triplicate on different days.

R. oryzae-induced endothelial or CHO cell damage was quantified by using a chromium ($^{51}$Cr) release assay (Ibrahim et al., J Infect Dis. 198(7):1083-1090 (2008)). Briefly, endothelial cells or CHO cells grown in 96-well tissue culture plates containing detachable wells were incubated with 1 µCi per well of Na$_2$$^{51}$CrO$_4$ (ICN) in M-199 medium (for endothelial cells) or Alpha minimum Eagle's medium (for CHO cells) for 16 hours.

On the day of the experiment, the unincorporated $^{51}$Cr was aspirated, and the wells were washed twice with warmed HBSS (Irvine Scientific). Cells were infected with fungal germlings ($1.5 \times 10^5$ germinated for 1 hour) suspended in 150 µl RPMI 1640 medium (Irvine Scientific) supplemented with glutamine. Spontaneous $^{51}$Cr release was determined by incubating endothelial or CHO cells in RPMI 1640 medium supplemented with glutamine without R. oryzae. After 3 hours of incubation at 37° C. in a 5% $CO_2$ incubator, 50% of the medium was aspirated from each well and transferred to glass tubes, and the cells were manually detached and placed into another set of tubes. The amount of $^{51}$Cr in the aspirate and the detached well was determined by gamma counting. The total amount of $^{51}$Cr incorporated by endothelial cells in each well equaled the sum of radioactive counts per minute of the aspirated medium plus the radioactive counts of the corresponding detached wells. After the data were corrected for variations in the amount of tracer incorporated in each well, the percentage of specific endothelial cell release of $^{51}$Cr was calculated by the following formula: [(experimental release×2)−(spontaneous release×2)]/[total incorporation−(spontaneous release×2)]. Each experimental condition was tested at least in triplicate and the experiment repeated at least once.

For Ab blocking of adherence, endocytosis, or damage caused by R. oryzae, the assays were carried out as above except that endothelial cells were incubating with 50 µg anti-GRP78 or anti-p53 Ab (as an isotype matching control) (Santa Cruz Biotechnology Inc.) for 1 hour prior to addition of R. oryzae germlings. Similar experiments were carried out to determine the effect of anti-GRP78 Ab on A. fumigatus- and C. albicans-induced damage to endothelial cells, with the exception that the damage assay was carried out for 20 hours and 3 hours, respectively.

To determine the effects of chelating endothelial cell iron on interactions with R. oryzae, endothelial cells were incubated with different concentrations of phenanthroline for 16 hours. To prevent chelation of the radioisotope, $^{51}$Cr was added to endothelial cells 24 hours prior to the addition of phenanthroline (Fratti et al., Infect Immun. 66(1):191-196 (1998)). To confirm that the effects of phenanthroline on R. oryzae-induced endocytosis by and damage of endothelial cells were due to chelation of endothelial cell iron, exogenous iron in the form of hemin was added to endothelial cells at a final concentration of 20 µM, 2 hours before phenanthroline (Fratti et al., supra). As a positive control for prevention of endocytosis, the microfilament disruptant cytochalasin D (Sigma-Aldrich) was added at a concentration of 200 nM simultaneously with R. oryzae germlings, and endocytosis was determined as above (Ibrahim et al., Infect Immun. 63(11):4368-4374 (1995)).

Transduction of Endothelial Cells with shRNA Lentiviral Particles.

The shRNA lentiviral particles, including TurboGFP control (SHC003V), non-target control (SHC002V), and GRP78 target (TRCN01024) were purchased from Sigma-Aldrich. The non-target control contains a scrambled sequence (CAA-CAAGATGAAGAGCACCAA (SEQ ID NO: 2)) not targeting any known human gene, while lentiviruses targeting the GRP78 gene contain sequence CTTGTTGGTGGCTC-GACTCGA (SEQ ID NO: 1).

The transductions were performed according to the manufacturer's protocol. Briefly, $1.6 \times 10^4$ endothelial cells were seeded into 96-well plate and incubated for about 20 hours at 37° C. in a 5% $CO_2$ incubator. Cells were infected with lentiviral particles at an MOI of 20 in the presence of 8 µg/ml polybrene (Sigma-Aldrich) overnight. The transduced cells were incubated in fresh M199 medium for 4 more days. Puromycin at 0.2 µg/ml was added to select for puromycin-resistant cell pools, which usually took approximately 10 days of incubating at 37° C. in 5% $CO^2$. The puromycin-resistant cells were passaged until an appropriate amount of cells was obtained for endocytosis or damage assays as above. Reduction of GRP78 expression was confirmed by using real time RT-PCR (see below).

Quantification of GRP78 Expression.

For quantification of GRP78 expression in endothelial or CHO cells, real time RT-PCR was carried out using a Power SYBR Green Cells-to-CT kit (Applied Biosystems) to extract RNA from $2 \times 10^4$ cells. Primers to amplify GRP78 from endothelial cells and CHO cells were 5'-GGAAAGAAGGT-TACCCATGC-3' (SEQ ID NO: 3) and 5'-AGAAGAGACA-CATCGAAGGT-3' (SEQ ID NO: 4). Primers 5'-ACCATCT-TCCAGGAGCGAG-3' (SEQ ID NO: 5) and 5'-TAAGCAGTTGGTGGTGCAG-3' (SEQ ID NO: 6) were used to amplify the housekeeping gene GAPDH, which was used as a control.

Effect of Acidosis, Iron, Glucose, Mannitol, and Statins on R. oryzae-Endothelial Cell Interactions.

To study the effect of acidosis, endothelial cells exposed to different pHs, ranging from 6.8 to 7.4, were grown in MEM buffered with HEPES for 5 hours in the presence or absence of phenanthroline. Next, endothelial cells were washed twice with cold PBS, and GRP78 total expression was quantified by real-time RT-PCR. To study the effect of glucose and iron on endothelial cell GRP78 expression levels and subsequent interactions of endothelial cells with R. oryzae germlings, we incubated endothelial cells in MEM with varying $FeCl_3$ or glucose concentrations for 5 hours or 20 hours, respectively (pilot studies demonstrated maximum enhancement of GRP78 expression at these time points). To study the effect of hyperosmolarity and statins on GRP78 expression, endothelial cells in MEM were incubated with 1, 4, or 8 mg/ml mannitol or 5, 20, or 40 µg/ml lovastatin for 20 hours. MEM did not have any glutamate, since this acid was found to induce expression of GRP78 (Yu et al., Exp Neurol. 155(2): 302-314 (1999)). GRP78 expression, endocytosis, and damage assays were conducted as above.

Cell surface expression of GRP78 on endothelial cells exposed to varying concentrations of $FeCl_3$ was quantified using FACS analysis. Briefly, endothelial cells grown in 25-cm flasks were dissociated using 1.5 ml enzyme-free dissociation buffer (Invitrogen). Cells were blocked with 50% goat serum, then stained with monoclonal anti-GRP78 Ab (BD Biosciences) at 1:100 for 1 hour. Endothelial cells were counterstained with ALEXA FLUOR 488-labeled anti-mouse IgG at 1:100 for 1 hour. Endothelial cells exposed to a similar concentration of $FeCl_3$ or glucose and stained with an isotype matching control IgG (BD Biosciences) were used as negative control. A FACSCaliber (BD) instrument equipped with an argon laser emitting at 488 nm was used for flow cytometric analysis. Fluorescence data were collected with logarithmic amplifiers. The population percent fluorescence of $5 \times 10^3$ events was calculated using CellQuest software (BD).

In Vivo Studies.

For in vivo studies, DKA was induced in BALB/c male mice ($\geq 20$ g) (National Cancer Institute) with a single i.p. injection of 190 mg/kg streptozotocin in 0.2 ml citrate buffer 10 days prior to fungal challenge (Ibrahim et al., *Antimicrob Agents Chemother.* 47(10):3343-3344 (2003)). Glycosuria and ketonuria were confirmed in all mice 7 days after streptozotocin treatment. To determine the available serum iron in DKA versus normal mice, serum samples were obtained from mice (n=11) and the serum iron levels measured using the method of Artis et al. (Artis et al., *Diabetes* 31(12):1109-1114 (1982)).

For quantification of GRP78 expression in mouse organs, lungs, brain, or sinus from normal or DKA mice were harvested 14 days following DKA induction (Ibrahim et al., *Antimicrob Agents Chemother.* 47(10):3343-3344 (2003)). Organs were stored in RNAlater solution (Ambion). Approximately 25 mg of brain or lung tissues was processed for RNA extraction using the RNAqueous-4PCR Kit (Ambion). Sinus bone was homogenized in liquid nitrogen (Fu et al., *FEMS Microbiol Lett.* 235(1):169-176 (2004).), and RNA was extracted using the QIAGEN RNeasy Kit. For mouse GRP78 expression, primers 5'-TCTTGCCATTCAAGGTGGTTG-3' (SEQ ID NO: 7) and 5'-TTCTTTCCCAAATACGCCTCAG-3' (SEQ ID NO: 8) were used, while primers to amplify the housekeeping gene GAPDH were as above. Calculations and statistical analyses were carried out as described in ABI PRISM 7000 Sequence Detection System User Bulletin 2 (Applied Biosystems).

To generate immune serum for passive immunization, normal BALB/c mice were immunized by s.c. injection of 20 μg recombinant hamster GRP78 (which is more than 98% identical to murine or human GRP78) mixed with CFA (Sigma-Aldrich) or with CFA alone mixed with PBS to generate non-immune control serum (Ibrahim et al., Infect Immun. 73(2):999-1005 (2005); Spellberg et al., *J Infect Dis.* 194(2):256-260 (2006)). Mice were boosted in incomplete Freund's adjuvant (IFA) 3 weeks later. Twelve days after the boost, serum was collected from GRP78-immunized or control mice (i.e., mice vaccinated with CFA/IFA without GRP78). Anti-GRP78 Ab titers were determined by using ELISA plates coated with 5 μg/ml of recombinant hamster GRP78 as previously described (Ibrahim et al., (2005) supra). Immune or control sera (0.25 ml) were administered i.p. to DKA recipient mice 2 hours before intranasal infection with $10^5$ *R. oryzae* 99-880 spores. Sera doses were repeated 3 days after infection, and survival of mice was followed for 90 days after infection. All procedures involving mice were approved by the Institutional Animal Use and Care Committee of the Los Angeles Biomedical Research Institute at Harbor—UCL Medical Center, according to the NIH guidelines for animal housing and care.

Statistics.

Differences in GRP78 expression and fungi—endothelial cell interactions were compared by the nonparametric Wilcoxon rank-sum test. The nonparametric log-rank test was used to determine differences in survival times. Comparisons with P values less than 0.05 were considered significant.

GRP78 Binds to Mucorales Germlings but not Spores.

Because *R. oryzae* is likely to interact with endothelial cells in the germling form during angioinvasion (Ibrahim et al., *Infect Immun.* 73(2):778-783 (2005)), we used the affinity purification process developed by Isberg and Leong (Isberg and Leong, *Cell* 60(5):861-871 (1990)) to identify an endothelial cell receptor for *R. oryzae* germlings. When incubated with extracts of endothelial cell membrane proteins, *R. oryzae* bound to a major band at 78 kDa. Lesser and inconsistent binding was found to a band at approximately 70 kDa and bands between 100-150 kDa (FIG. 1A).

The major band at 78 kDa that bound to germlings was excised for protein identification by matrix-assisted laser desorption/ionization—time-of-flight tandem mass spectrometry (MALDI-TOF MS/MS) analysis. Several potential matches were identified, including human glucose-regulated protein 78 (GRP78). GRP78 was selected for further investigation due to its expression being likely regulated in DKA. To verify that endothelial cell GRP78 bound *R. oryzae* germlings, immunoblots containing endothelial cell membrane proteins were probed with an anti-GRP78 polyclonal Ab raised against a synthetic peptide corresponding to amino acids 24-43 of human GRP78. This polyclonal Ab recognized the germling-bound 78-kDa band (FIG. 1B). Time course studies revealed that GRP78 was bound by germlings after 1-3 hours of germination but not by *R. oryzae* spores (FIG. 1C). Finally, endothelial cell GRP78 bound to germlings of other Mucorales family members that are known to cause mucormycosis, including another strain of *R. oryzae*, and strains of *Rhizopus microsporus, Mucor* species, and *Cunninghamella* species.

Figure 2:
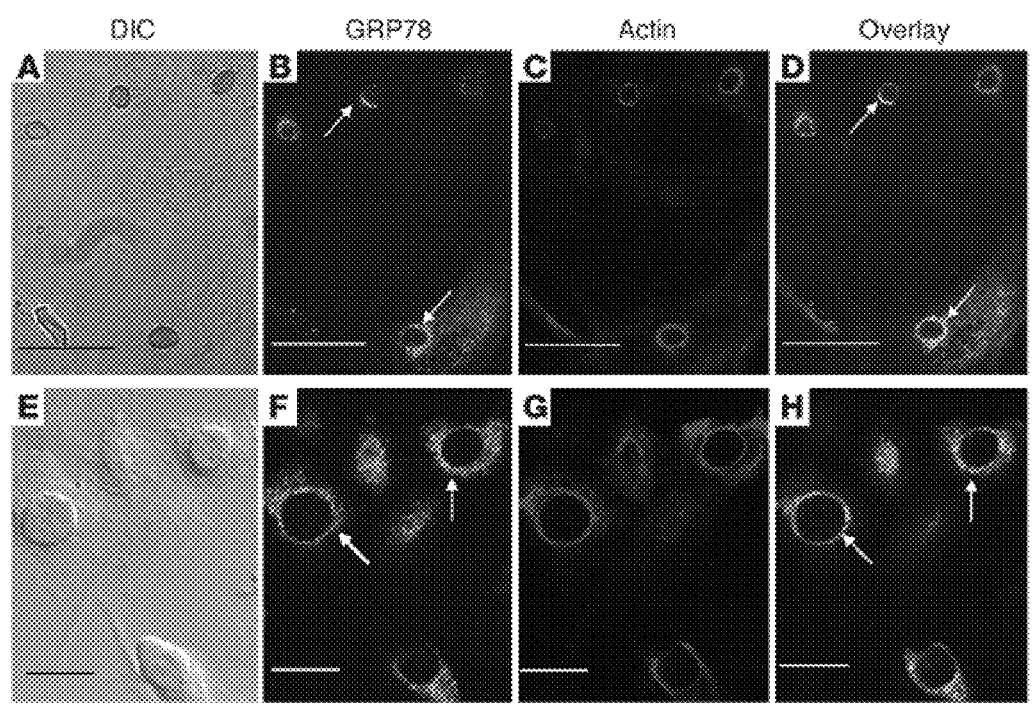
FIG. 2, panels A-H, show GRP78 on intact endothelial cells co-localizes with R. oryzae germlings that are being endocytosed. Panels A-D are confocal microscopic images of endothelial cells infected with R. oryzae cells that have been germinated for 1 hour. Panels E-H are confocal microscopic images of endothelial cells infected with R. oryzae cells that have been germinated for 2 hours. Confluent endothelial cells on a 12-mm-diameter glass coverslip were infected with $10^5$/ml R. oryzae germlings. After 60-minute incubation at 37° C., the cells were fixed with 3% paraformaldehyde, washed, blocked, and then permeabilized as described in Phan et al., J Biol Chem 280(11):10455 (2005). The cells were stained with GRP78 using rabbit anti-GRP78 polyclonal Ab (Abeam), followed by a counterstain with goat anti-rabbit IgG conjugated with ALEXA FLUOR 488 (Molecular Probes, Invitrogen) (Panels B and F). To detect F-actin, the cells were incubated with ALEXA FLUOR 568-labeled phalloidin (Molecular Probes) per the manufacturer's instructions (Panels C and G). A merged image is shown in Panels D and H. Panels A and E are the same fields taken with differential interference contrast imaging. Arrows indicate GRP78 and microfilaments that have accumulated around R. oryzae. Scale bars: 30 µm (Panels A-D) and 20 µm (Panels E-H).

Indirect immunofluorescence was used to verify that GRP78 on intact endothelial cells was bound by *R. oryzae*. Endothelial cells expressed GRP78 on the cell surface (FIG. 2, B and F), in accordance with previous reports (Li and Lee, *Curr Mol Med.* 6(1):45-54 (2006); Davidson et al., *Cancer Res.* 65(11): 4663-4672 (2005)). When endothelial cells were infected with *R. oryzae* germlings, GRP78 colocalized with *R. oryzae* (FIG. 2, D and H). These fungal cells were being endocytosed because they were surrounded by endothelial cell microfilaments (FIG. 2, C and G). These findings confirm that during endocytosis, *R. oryzae* germlings bind to GRP78 on intact endothelial cells.

GRP78 is a Receptor for *R. oryzae* Germlings.

Figure 3:
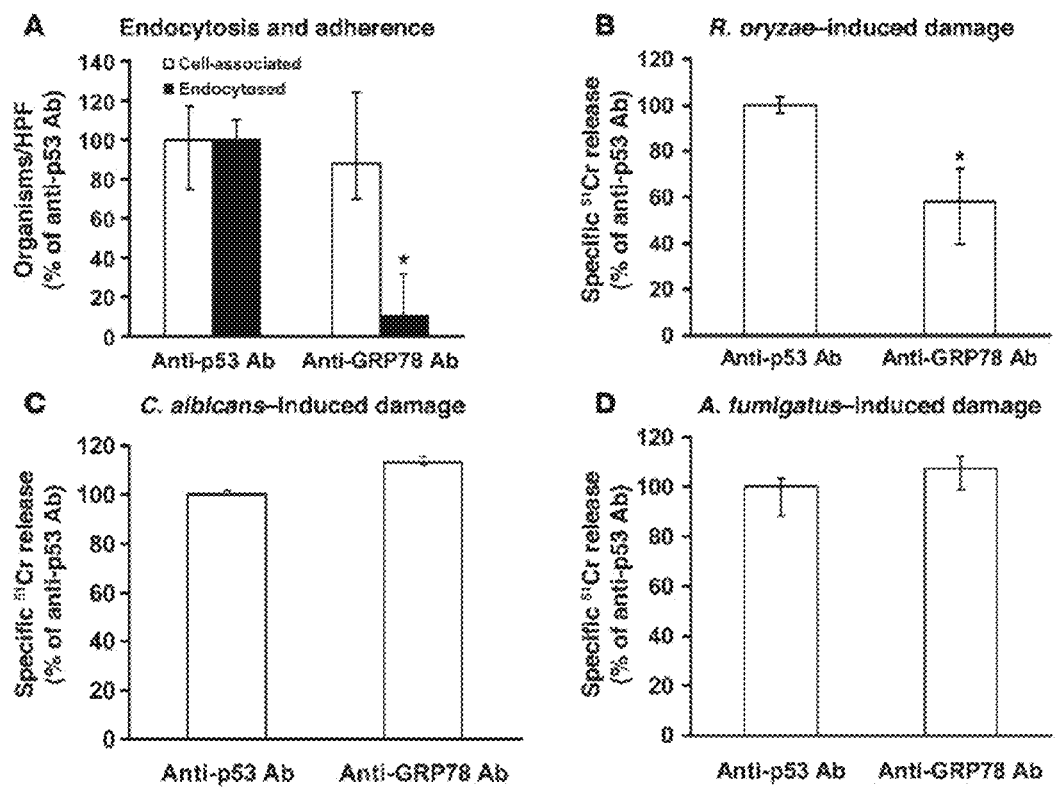
FIG. 3, panels A-D, show anti-GRP78 Ab blocks endothelial cell endocytosis of and damage by R. oryzae but not damage caused by C. albicans or A. fumigatus. Adherence and endocytosis (determined by differential fluorescence) assays were carried out using endothelial cells split on 12-mm glass coverslips, while damage was carried out using the 96-well plate $^{51}Cr$ release method. Endothelial cells were incubated with 50 µg/ml anti-GRP78 or anti-p53 Ab (control) (Santa Cruz Biotechnology Inc.) for 1 hour prior to addition of R. oryzae germlings. Blocking of GRP78 with Ab abrogates endocytosis of R. oryzae by endothelial cells (data derived from >700 fungal cells interacting with approximately 200 endothelial cells/each group/experiment, with an average of 59% cells being endocytosed in the control) (Panel A) and reduces the ability of the fungus to cause endothelial cell damage (Panel B). However, anti-GRP78 Ab did not block damage caused by C. albicans (Panel C) or A. fumigatus (Panel D). *$P<0.01$ compared with anti-p53 Ab by Wilcoxon rank-sum test. n=6 slides per group from 3 independent experiments for endocytosis, and n=6 wells per group from 2 independent experiments for damage assay. Data are expressed as median±interquartile range.

Because endocytosis of the fungus is a prerequisite for *R. oryzae* to cause endothelial cell damage (Ibrahim et al., (2005) supra), whether blocking the function or expression of GRP78 would protect endothelial cells from *R. oryzae*-induced endocytosis and subsequent damage was determined. Endocytosis, but not adherence, of *R. oryzae* germlings was abrogated by addition of an anti-GRP78 but not control polyclonal Ab, the latter of which targeted p53, which is not expressed by endothelial cells (FIG. 3A). The anti-GRP78 Ab reduced by more than 40% damage to endothelial cells caused by *R. oryzae* germlings (FIG. 3B) but not *Candida albicans* (FIG. 3C) or *Aspergillus fumigatus* (FIG. 3D).

Figure 4:
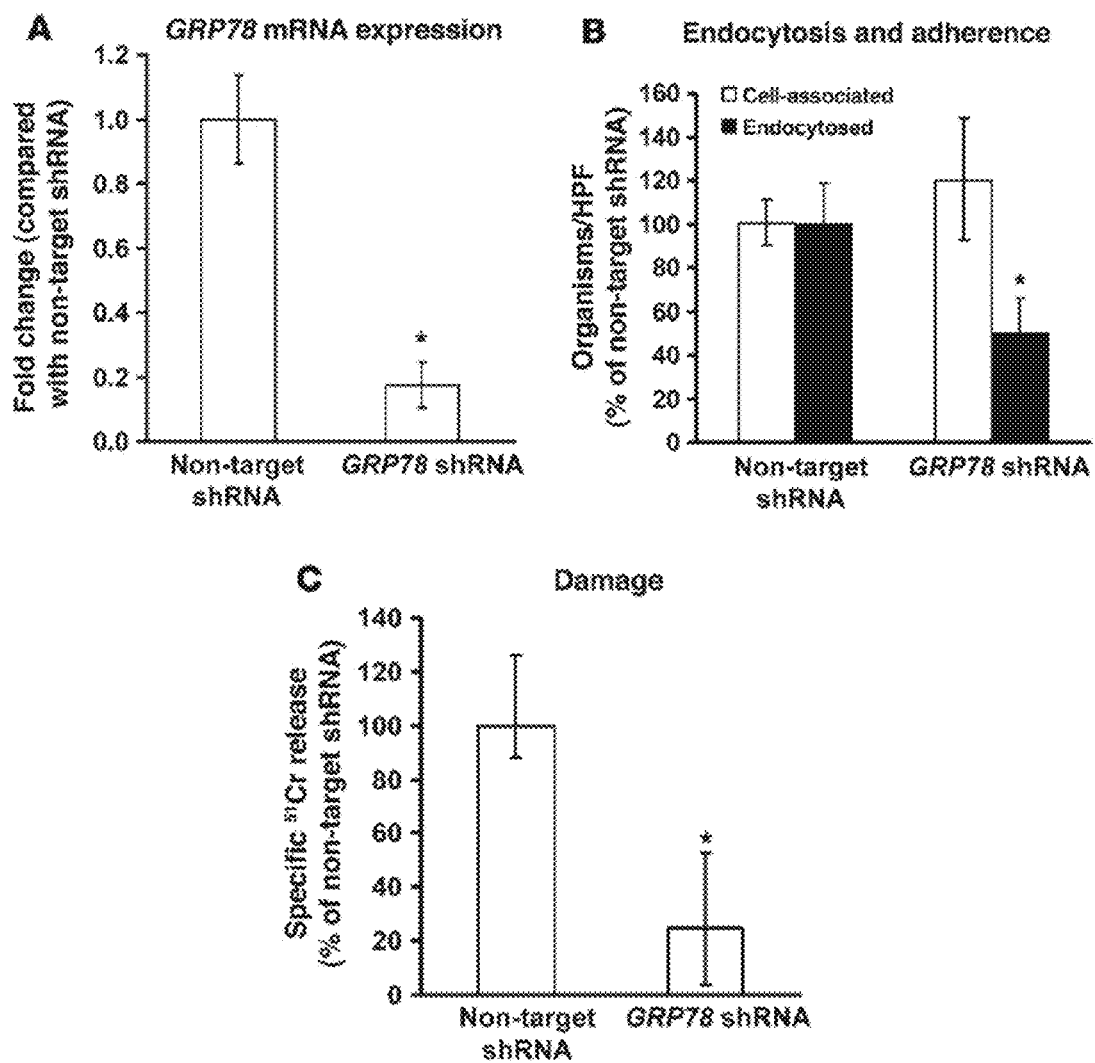
FIG. 4, panels A-C show downregulation of endothelial cell GRP78 expression with siRNA reduces the number of endocytosed organisms and subsequent damage to endothelial cells. Endothelial cells were transduced with lentivirus containing either shRNA targeting GRP78 or a scrambled sequence (Non-target shRNA). Transduction of endothelial cells with GRP78 shRNA lentiviruses reduced GRP78 transcript levels (Panel A), diminished the number of endocytosed R. oryzae germlings (data derived from >800 fungal cells interacting with approximately 250 endothelial cells/each group/experiment, with an average of 76% being endocytosed in the non-target shRNA) (Panel B), and blocked R. oryzae-induced endothelial cell damage (Panel C). *$P<0.005$ compared with non-target shRNA by Wilcoxon rank-sum test for all comparisons. n=6 slides per group from 3 independent experiments for endocytosis, and n=6 wells per group from 2 independent experiments for damage assay. Data are expressed as median±interquartile range.

To complement the Ab blocking studies, GRP78 expression was suppressed to determine its impact on adherence, endocytosis, and endothelial cell damage. Because GRP78 is essential (Luo et al., *Mol Cell Biol.* 26(15):5688-5697 (2006)), shRNA was used to downregulate its expression. Transduction of endothelial cells with a lentivirus containing GRP78 shRNA mediated an 80% reduction in GRP78 transcript levels compared with endothelial cells transduced by non-target shRNA lentivirus (FIG. 4A). This suppression of GRP78 expression resulted in a significant reduction in endothelial cell endocytosis of *R. oryzae* germlings and subsequent endothelial cell damage (FIG. 4, B and C). Collectively, these results show that GRP78 is essential for maximal endocytosis of *R. oryzae* germlings by endothelial cells.

Figure 5:
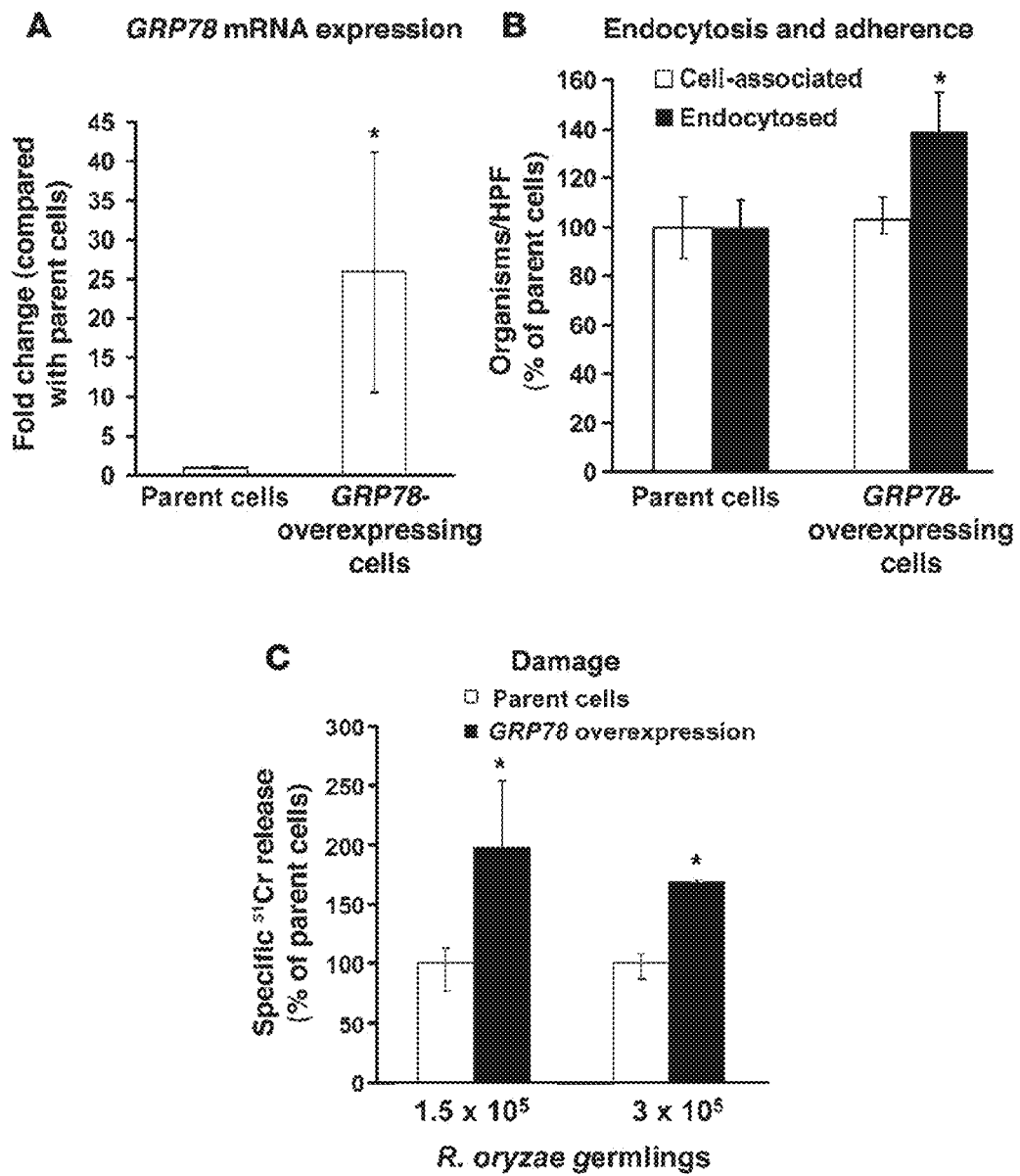
FIG. 5, panels A-C, show heterologous overexpression of GRP78 in CHO cells makes them more susceptible to *R. oryzae*-induced invasion and subsequent damage. The C.1 cell line, which was derived from parental DHFR-deficient CHO cells engineered to overexpress GRP78, was found to overexpress GRP78 (Panel A). *P=0.01 compared with parent cells by nonparametric Wilcoxon rank-sum test; n=6 per each group. C.1 cells were able to endocytose more *R. oryzae* germlings (data derived from >950 fungal cells interacting with approximately 300 CHO cells/each group/experiment, with an average of 40.9% being endocytosed in the parent cells) (Panel B) and were more susceptible to *R. oryzae*-induced damage (Panel C). *P<0.005 compared with parent cells by Wilcoxon rank-sum test. n=6 slides per group from 3 independent experiments for endocytosis, and n=6 wells per group from 2 independent experiments for damage assay. Data are expressed as median±interquartile range.

As an additional confirmatory method, the cell line C.1 was used, which was derived from parental dihydrofolate reductase-deficient (DHFR-deficient) CHO cells engineered to overexpress hamster GRP78 (Reddy et al., *J Biol Chem.* 278(23):20915-20924 (2003); Morris et al., *J Biol Chem.* 272(7):4327-4334 (1997)). C.1 cells overexpressed GRP78 transcript by 26-fold compared with their parent cells (FIG. 5A). The C.1 cells had a 40% increase in endocytosis of *R. oryzae* germlings, which resulted in a more than 50% increase in damage (FIG. 5, B and C) compared with the parent CHO cells, which do not overexpress GRP78. These results were specific to *R. oryzae* germlings, because CHO cells overexpressing GRP78 had no effect on endocytosis of *R. oryzae* spores, which do not bind GRP78 (data not shown). Thus, the enhanced endocytosis of germlings induced by GRP78 overexpression is not the result of a generalized increase in endocytosis. These results show that GRP78 functions as an endothelial cell receptor for *R. oryzae* germlings.

Iron Regulates Endothelial Cell Damage by *R. oryzae*.

Figure 6:
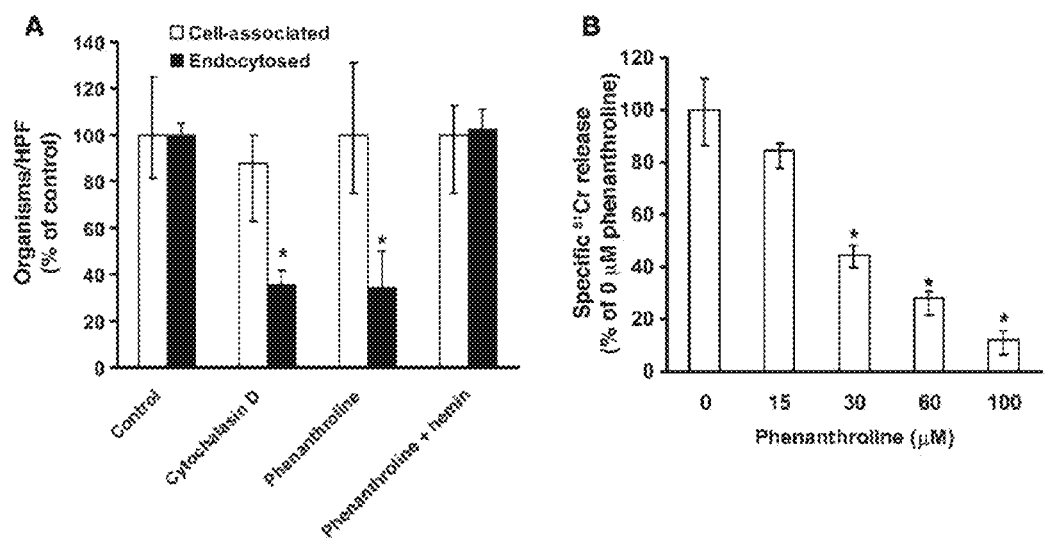
FIG. 6, panels A and B, show chelation of endothelial cell iron protects them from invasion and subsequent injury by *R. oryzae*. Panel A) Endothelial cells were incubated with the iron chelator phenanthroline (60 µM), cytochalasin D (200 nM), or phenanthroline saturated with Hemin (20 µM) for 16 hours, then the cells were rinsed and processed for endocytosis and adherence (data derived from >400 fungal cells interacting with approximately 150 endothelial cells/each group/experiment, with an average of 77% being endocytosed in the control). Panel B) Endothelial cells were treated with varying concentrations of phenanthroline for 16 h then the iron chelator was removed prior to carrying out *R. oryzae*-induced endothelial cell injury as above. *p<0.001 vs. control (*R. oryzae* germlings without phenanthroline), by Wilcoxon Rank Sum test. n=6 slides per group from 3 independent experiments for endocytosis, and n=8 wells per group from 2 independent experiments for damage assay. Data are expressed as medians+interquartile ranges.

Patients with elevated available serum iron, such as DKA patients (Artis et al., *Diabetes* 31(12):1109-1114 (1982)) or those treated with deferoxamine (an iron siderophore that provides *Rhizopus* with exogenous iron) (Boelaert et. al., *J Clin Invest.* 91(5):1979-1986 (1993)), are uniquely predisposed to developing mucormycosis. Furthermore, the iron chelator deferasirox, which reduces available serum iron, is effective in treating experimental hematogenously disseminated mucormycosis (Ibrahim et al., *J Clin Invest.* 117(9): 2649-2657 (2007)). Given the role of iron in the pathogenesis of mucormycosis infections, we sought to define the impact of iron levels on endothelial cell endocytosis of *R. oryzae*. Endothelial cell adherence, endocytosis, and damage caused by *R. oryzae* were compared following exposure to phenanthroline (an iron chelator) with or without exogenous iron. As a positive control, *R. oryzae* germlings were incubated on endothelial cells that were exposed to the microfilament disruptant cytochalasin D, which prevents endocytosis (Ibrahim et al., *Infect Immun.* 63(11):4368-4374 (1995)). None of the treatments altered fungal adherence to endothelial cells (FIG. 6A). However, similar to cytochalasin D, phenanthroline reduced endothelial cell endocytosis of *R. oryzae* by approximately 70% (FIG. 6A). Further, the addition of exogenous iron completely reversed the inhibition of endocytosis caused by the iron chelator. Finally, phenanthroline prevented *R. oryzae*-induced endothelial cell damage in a concentration-dependent manner (FIG. 6B). Thus, iron regulates the susceptibility of endothelial cells to damage caused by *R. oryzae* by modulating endocytosis of the organism.

Figure 7:
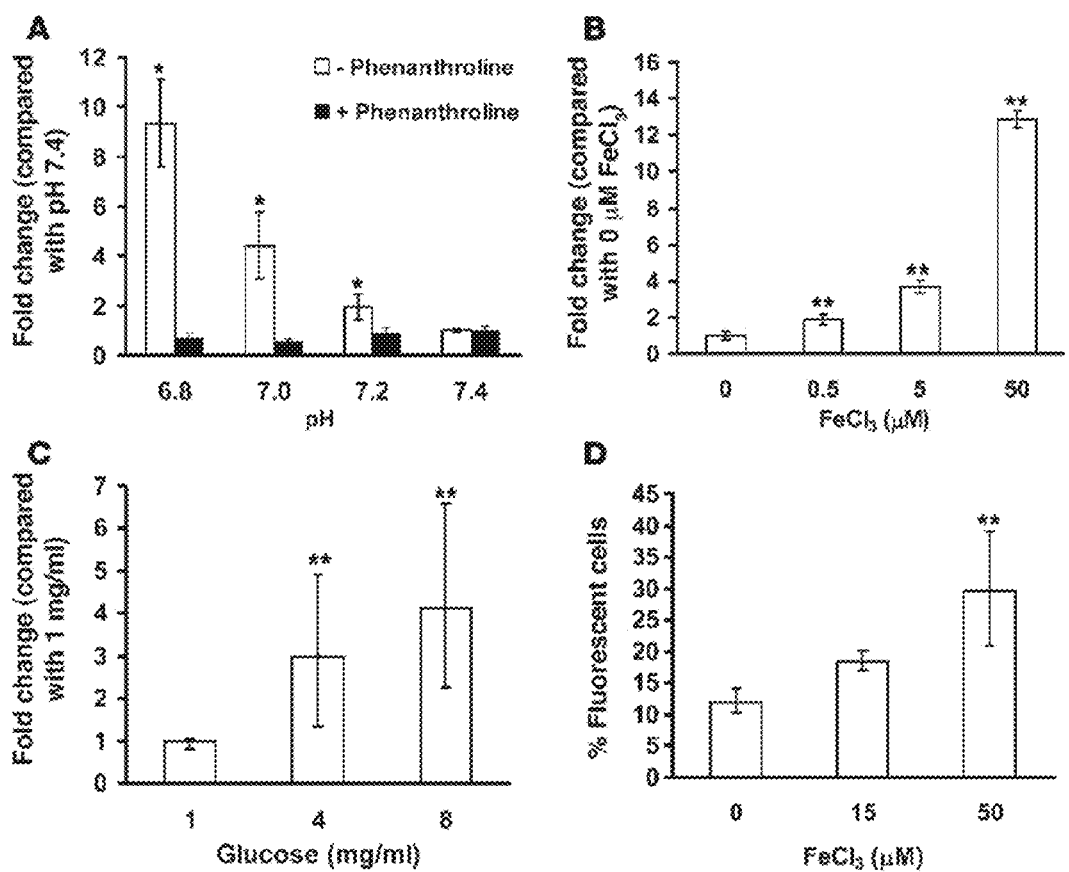
FIG. 7, panels A-D, show acidosis as well as iron and glucose concentrations consistent with those seen in DKA patients induce expression of GRP78. Endothelial cells were incubated at various pHs with or without phenanthroline (Panel A), with iron (Panel B) or glucose (Panel C) concentrations often seen in DKA patients for 5 hours (for studying the effect of acidosis or iron) or 20 hours (for studying the effect of glucose), then the expression of GRP78 was quantified by real-time RT-PCR. n=6 wells per group from 2 independent experiments. Data are expressed as median±interquartile range. Cell surface expression of GRP78 on endothelial cells (n=4 per group from 2 independent experiments) exposed to $FeCl_3$ was quantified using FACS analysis following staining with anti-GRP78 mAb, then counterstaining with anti-mouse ALEXA FLUOR 488-labeled Ab (Panel D). Data are presented as percent of median fluorescent cells±interquartile range. *P<0.01 versus pH 7.4 or the same pH with phenanthroline; **P<0.05 versus 1 mg/ml glucose or 0 $FeCl_3$ by Wilcoxon rank-sum test.

Iron and glucose are inducers of GRP78. Patients with DKA have elevated levels of available serum iron, likely due to release of iron from binding proteins in the presence of acidosis (Artis et al., supra). High iron and glucose concentrations similar to those seen in DKA patients induce expression of GRP78, make the host more susceptible to mucormycosis. This is confirmed by the acidosis affects on the expression of GRP78 through an iron-related mechanism. Endothelial cells were incubated at pH values similar to those seen in patients with DKA, and their GRP78 expression was quantified by real-time RT-PCR. Lower pH values significantly enhanced expression of endothelial cell GRP78 compared with the normal blood pH of 7.4 (FIG. 7A). Furthermore, addition of the iron chelator phenanthroline in the setting of acidosis reversed GRP78 expression back to normal levels seen with pH 7.4, indicating that the impact of acidosis is to release free iron from iron-binding proteins and that the increased free iron is the direct mediator of GRP78 expression.

To further study the role of iron and glucose directly on endothelial cell GRP78 expression, endothelial cells were incubated in increasing concentrations of $FeCl_3$ and glucose for varying time intervals and quantified the level of GRP78 transcript by real-time RT-PCR. Endothelial cells incubated with concentrations of iron present in sera collected from patients with DKA (Ards et al., supra) induced up to a 12-fold increase in endothelial cell GRP78 expression compared with endothelial cells incubated with no iron (FIG. 7B). Similarly, incubating endothelial cells with glucose at 4 or 8 mg/ml led to a 3- or 4-fold increase in mRNA expression of GRP78, respectively, compared with cells incubated in a normal physiological concentration of glucose (1 mg/ml, P=0.005) (FIG. 7C). To discern whether GRP78 overexpression in response to glucose was due to hyperglycemia itself, or rather to hyperosmolarity caused by the increased glucose, the expression of GRP78 was measured after incubating endothelial cells with similar concentrations of mannitol (i.e., 1, 4, and 8 mg/ml) for 20 hours. No change in GRP78 expression was noticed (data not shown), indicating that hyperglycemia and not hyperosmolarity is responsible for the enhanced GRP78 expression. Because HMG-CoA reductase inhibitors (i.e., statins) might affect mucormycosis incidence in diabetic patients (Kontoyiannis D P., *Clin Infect Dis.* 44(8):1089-1090 (2007)), the impact of lovastatin on GRP78 expression was tested. No evidence of alterations in expression in the presence of the statin was found (data not shown).

To confirm that the increased mRNA expression of GRP78 translated into increased protein surface expression, endothelial cells were incubated with 0, 15, or 50 µM $FeCl_3$, the latter of which mediated the strongest increase in mRNA transcription, and stained them with anti-GRP78 monoclonal Ab or isotype control. Fluorescence was quantified by flow cytometry. Surface expression of GRP78 protein increased by 150% in the presence of high iron levels (FIG. 7D).

Iron- and Glucose-Induced GRP78 Overexpression Enhances Susceptibility of Endothelial Cells to *R. oryzae*-Induced Invasion and Damage.

Figure 8:
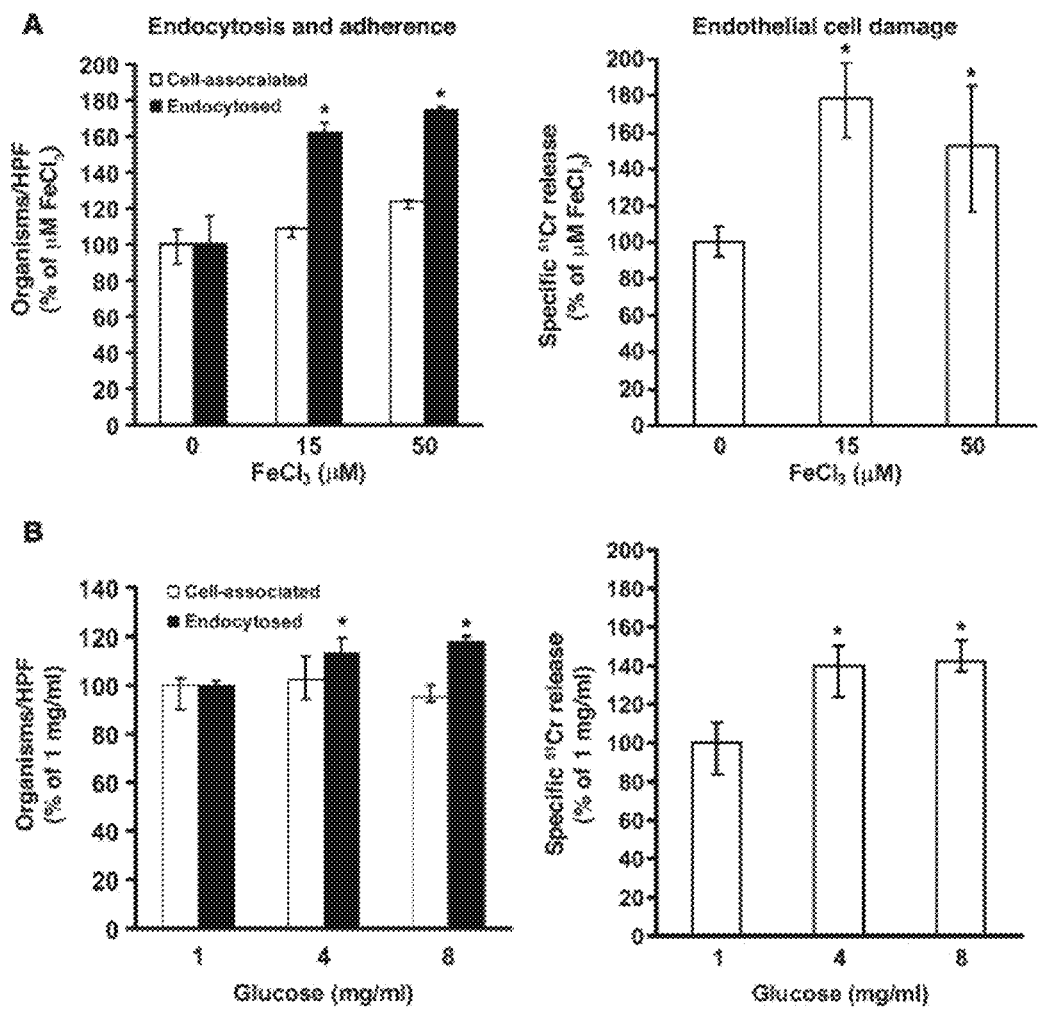
FIG. 8, panels A and B, show glucose and iron concentrations consistent with those seen in DKA patients induce expression of GRP78 and subsequent penetration of and damage to endothelial cells by *R. oryzae*. Endothelial cells exposed to high concentrations of iron (Panels in row A) or glucose (Panels in row B) were subsequently evaluated for their susceptibility to *R. oryzae*-mediated endocytose and damage. The endocytosis data were derived from more than 600 fungal cells interacting with approximately 200 endothelial cells/each group/experiment, with an average of 51% and 58% endocytosis for no $FeCl_3$ and 1 mg/ml glucose, respectively. *P<0.01 compared with no $FeCl_3$ or with 1 mg/ml glucose by Wilcoxon rank-sum test. n=6 slides per group from 3 independent experiments for endocytosis, and n=9 wells per group from 3 independent experiments for damage assay. Data are expressed as median±interquartile range.
Figure 9:
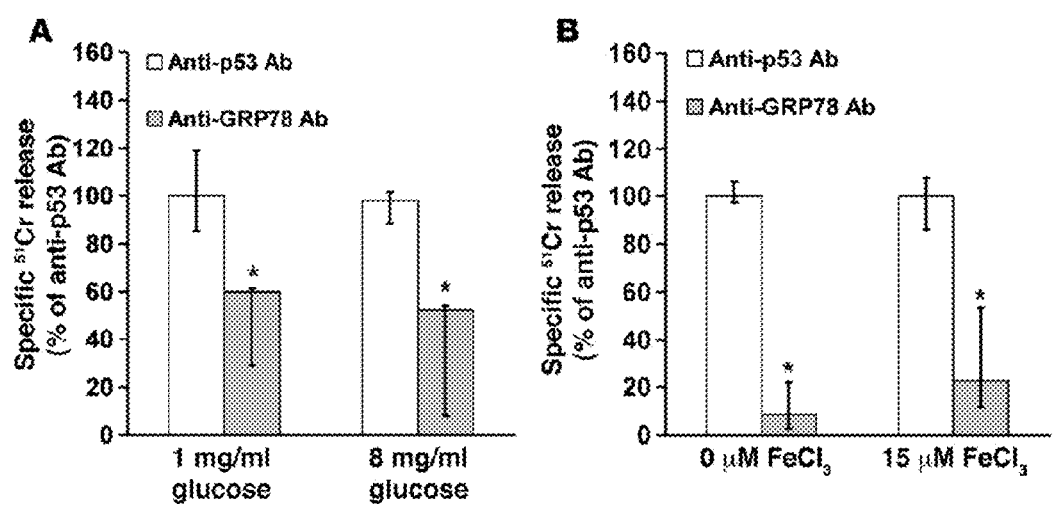
FIG. 9, panels A and B, show anti-GRP78 mAb blocked endothelial cell endocytosis of (see panel A) and subsequent damage by (see panel B) *R. oryzae*. Endothelial cells were incubated with *R. oryzae* in the presence of 50 µg anti-GRP78 Ab or anti-p53 Ab (control). The endocytosis data were derived from more than 500 fungal cells interacting with approximately 150 endothelial cells/each group/experiment, with an average of 71% endocytosis in the control. *P<0.02 versus anti-p53 Ab. n=6 slides per group from 3 independent experiments for endocytosis, and n=6 wells per group from 2 independent experiments for damage assay. Data are expressed as median±interquartile range.

Incubation of endothelial cells with either 15 or 50 µM $FeCl_3$ enhanced *R. oryzae*-induced endocytosis and subsequent damage by 80% compared with endothelial cells incubated without exogenous $FeCl_3$ (FIG. 8A). Similarly, incubation of endothelial cells with 4-8 mg/ml glucose resulted in approximately 20% and 40% increases in endocytosis of and damage caused by *R. oryzae*, respectively, when compared with endothelial cells incubated in 1 mg/ml glucose (FIG. 8B). Importantly, the anti-GRP78 Ab blocked this enhanced endothelial cell susceptibility to *R. oryzae*-induced damage, confirming the specificity of the increased susceptibility to overexpression of GRP78 (FIG. 9). Collectively, these results show that iron and glucose concentrations consistent with those seen in patients with DKA induce the overexpression of GRP78, resulting in enhanced endocytosis and damage of endothelial cells.

GRP78 During Mucormycosis In Vivo.

To determine the potential role for GRP78 in mediating susceptibility to mucormycosis in vivo, Grp78 expression was quantified by RT-PCR in mice with DKA (which, like humans, are hypersusceptible to mucormycosis) (Waldorf et al., *J Clin Invest.* 74(1):150-160 (1984)) and in normal mice. Mice were rendered diabetic with streptozotocin (Waldorf et al., supra; Ibrahim et al., *Antimicrob Agents Chemother.*

Figure 10:
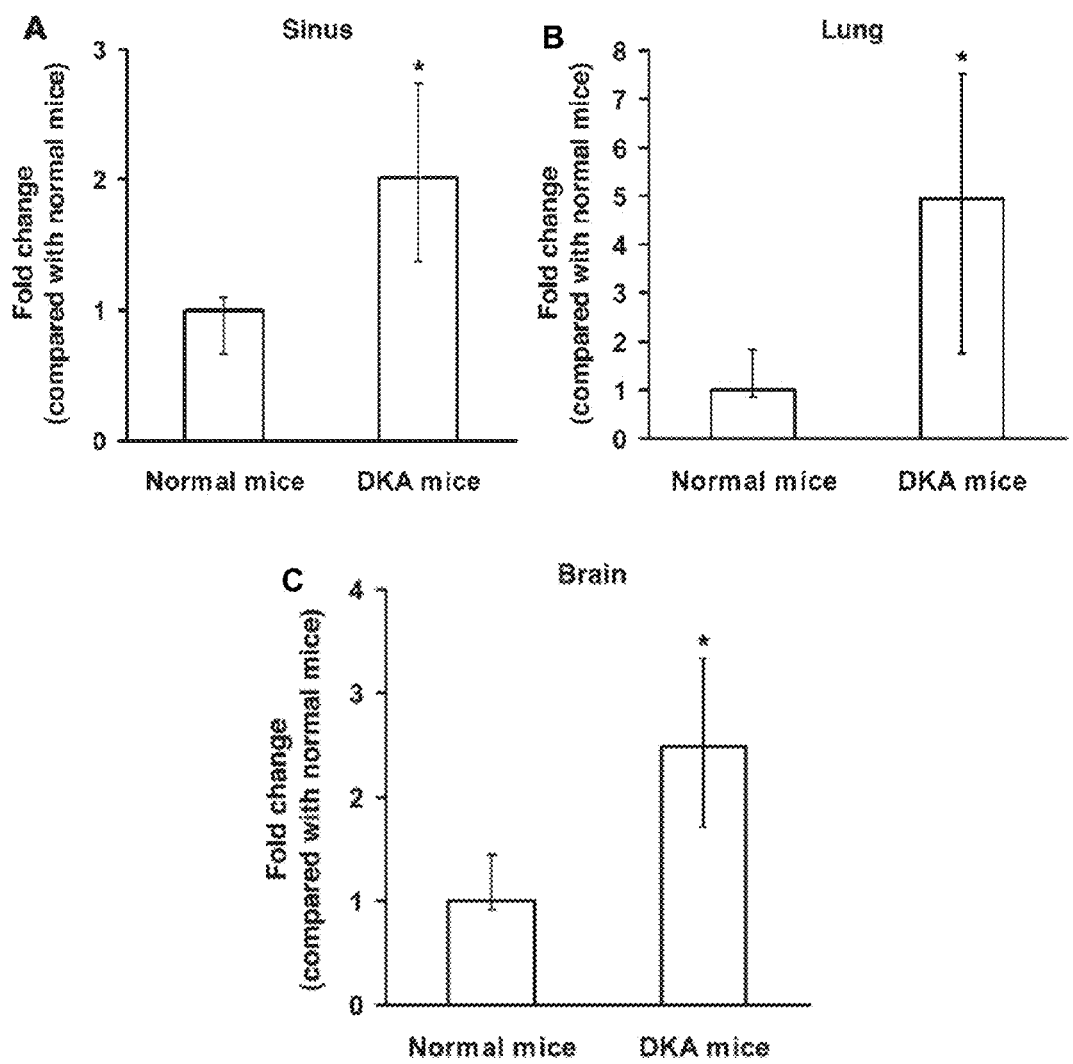
FIG. 10, panels A-C, show GRP78 is overexpressed in various tissues of DKA mice and anti-GRP78 immune serum protects mice from mucormycosis. Different organs harvested from DKA or normal mice (n=7 per arm) were processed for GRP78 quantification by real time RT-PCR. Panels A-C shows GRP78 expression in sinus tissue, lung tissue, and brain tissue, respectively. *p<0.05 compared to normal mice. Data are expressed as medians+interquartile ranges.

47(10):3343-3344 (2003)). Diabetes was confirmed by measurement of increased urinary glucose levels. Concordant with the establishment of DKA, diabetic mice had a decrease in blood pH from 7.8 (normal for mice) to 7.3-7.2, associated with increased levels of urinary glucose (250-1,000 mg/dl) and urinary ketone bodies (≥5 mg/dl) as determined by Keto-Diastix strip testing. We also compared levels of serum-free iron (i.e., unbound by carrier proteins such as transferrin) in DKA mice with those in normal mice. In accordance with the results found in humans (Artis et al., supra), DKA mice (n=11) had approximately 5-fold-higher levels of serum-free iron than normal mice (median[25th quartile, 75th quartile], 7.29 [4.3, 11.8] µM vs. 1.69 [1.3, 2.3] µM; P=0.03 by Wilcoxon rank-sum test). Finally, concordant with the regulation of GRP78 expression by iron and glucose levels, DKA mice were found to express 2- to 5-fold-higher levels of Grp78 mRNA in sinus, lungs, and brain compared with normal mice (FIG. 10A-C).

Figure 11:
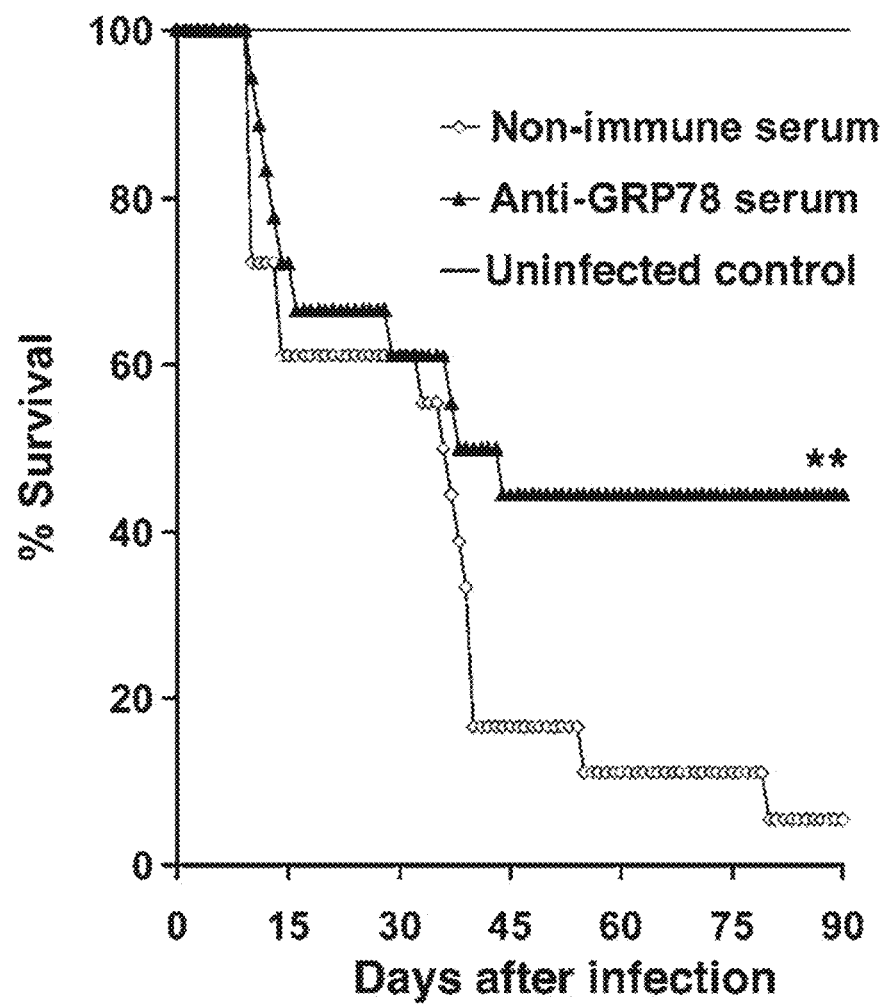
FIG. 11 shows anti-GRP78 immune serum protects mice from mucormycosis. Survival of mice (n=18, from 2 independent experiments with similar results) infected intranasally with *R. oryzae* ($10^5$ spores actual inoculum) and treated with anti-GRP78 immune or non-immune sera. **p=0.037 by log-rank test. The experiment was terminated on day 90 with all remaining mice appearing healthy.

To determine the potential for abrogation of GRP78 function as a treatment for mucormycosis, female BALB/c mice were vaccinated with recombinant hamster GRP78 (which is more than 98% identical to murine or human GRP78), and serum was collected from GRP78-immunized or control mice. The median anti-GRP78 Ab titer of serum collected from vaccinated mice was found to be 1:128,000 compared with a titer of 1:600 in the serum collected from mice vaccinated with adjuvant alone as determined by ELISA (P=0.005). The efficacy of the anti-GRP78 serum was compared with that of the non-immune serum in protecting naive mice from $R.\ oryzae$ infection. DKA mice were treated intraperitoneally with anti-GRP78 or non-immune serum 2 hours prior to intranasal infection with 105 spores of $R.\ oryzae$. Another dose of serum was given on day +3 relative to infection. DKA mice that received anti-GRP78 serum had marked improvement in survival compared with mice treated with non-immune serum (FIG. 11). Lungs and brains harvested from surviving mice were found to be sterile at the end of the experiment.

As evidenced by the experimental examples described herein, host GRP78 plays a critical role in susceptibility to mucormycosis and that increased GRP78 expression offers an explanation for the unique susceptibility to mucormycosis of hyperglycemic hosts with elevated available serum iron. While mucormycosis can occur in patients with profound neutropenia or those receiving high doses of corticosteroids (Spellberg et al., (2005) supra; Roden et al., $Clin\ Infect\ Dis.$ 41(5):634-653 (2005)), the most common risk factor for mucormycosis is diabetes (Spellberg et al., (2005) supra;, Ibrahim et al., (2008) supra). Although the attack rate of mucormycosis is substantially higher in patients with DKA than in diabetic patients who are not acidotic, less than half of diabetic patients with mucormycosis are acidotic (Roden et al., supra; Reed et al., $Clin\ Infect\ Dis.$ 47(3):364-371 (2008)). Therefore, diabetes is a risk for mucormycosis even in the absence of acidosis, but acidosis enhances the predisposition of diabetic patients to mucormycosis. The causes of this predisposition of patients with diabetes, and DKA in particular, to mucormycosis has never been adequately explained.

The results described herein elucidate the predisposition of diabetic and DKA patients to mucormycosis. GRP78 expression was enhanced in hosts with elevated available serum iron levels and high glucose concentrations, and this enhanced expression of GRP78 resulted in increased endocytosis of $R.\ oryzae$ by human endothelial cells and subsequent enhanced damage to the cells. Furthermore, suppression of GRP78 function by Ab and its reduced expression levels by shRNA blocked $R.\ oryzae$ uptake and resulting damage to human endothelial cells. In contrast, the anti-GRP78 Abs did not block fungal endothelial cell damage mediated by $C.\ albicans$ or $A.\ fumigatus$, two other fungal pathogens that do not have an increased attack rate in patients with DKA. These results clearly show that mice with DKA, which had elevated levels of glucose and available iron and overexpressed Grp78 in relevant target tissues, were protected from mucormycosis infection when the receptor was blocked by Abs. These exciting results demonstrate GRP78-blocking strategies can be used as a therapeutic intervention in treating or preventing mucormycosis.

Exposure to hyperglycemia of iron-sequestering proteins, such as apotransferrin and hemoglobin, has been shown to damage the proteins and cause them to release free iron in serum (Kar and Chakraborti, $Indian\ J\ Exp\ Biol.$ 37(2):190-192 (1999); van Campenhout et al., $Free\ Radic\ Res.$ 37(10):1069-1077 (2003)). Therefore, diabetes can result in increased serum-free iron even in the absence of acidosis. Furthermore, acidosis has been shown to markedly increase dissociation of iron from sequestering proteins in serum from DKA patients, independent of glucose levels (Artis et al., supra). The data presented herein confirms that hyperglycemia as well as increased iron levels in the absence of hyperglycemia increase expression of GRP78 in host cells. Thus, increased GRP78 expression caused by hyperglycemia results in the predisposition of non-acidotic diabetic patients to mucormycosis, whereas the potentiation of increased free iron levels caused by acidosis results in the marked increase in attack rate of mucormycosis in patients with DKA.

GRP78 (also known as BiP/HSPA5) was discovered as a cellular protein induced by glucose starvation (Lee A S, $Cancer\ Res.$ 67(8):3496-3499 (2007)). It is a member of the HSP70 protein family that is mainly present in the endoplasmic reticulum. It functions as a major chaperone that is involved in many cellular processes, including protein folding and assembly, marking misfolded proteins for proteosome degradation (Ni and Lee, $FEBS\ Lett.$ 581(19):3641-3651 (2007)), regulating $Ca^{2+}$ homeostasis, and serving as a sensor for endoplasmic reticulum stress (Li and Lee, $Curr\ Mol\ Med.$ 6(1):45-54 (2006)). GRP78 has also been reported to be antiapoptotic and plays critical cytoprotective roles in early embryogenesis, oncogenesis, neurodegenerative diseases, and atherosclerosis (Lee A S, $Cancer\ Res.$ 67(8):3496-3499 (2007)). More recently, GRP78 overexpression was shown to inhibit both insulin-dependent and endoplasmic reticulum stress-induced SREBP-1 activation, resulting in reduction of hepatic steatosis in obese mice (Kammoun et al., $J\ Clin\ Invest.$ 119(5):1201-1215 (2009)).

Despite its main function as a cellular chaperone protein, recent studies reported the translocation of a fraction of GRP78 to the cell surface in a variety of cells (Wang et al., $Antioxid\ Redox\ Signal.$ 11(9):2307-2316 (2009)). In fact, GRP78 has been reported to function as a receptor for a variety of ligands, including (a) the angiogenesis inhibitor Kringle 5 (Davidson et al., $Cancer\ Res.$ 65(11): 4663-4672 (2005)), (b) the activated proteinase inhibitor α2-macroglobulin (Misra et al., $Cell\ Signal$ 16(8):929-938 (2004)), (c) a synthetic 12-aa peptide (Hardy et al., $Biochem\ Pharmacol.$ 75(4):891-899 (2008)), (d) dengue virus serotype 2 (Jindadamrongwech et al., $Arch\ Virol.$ 149(5):915-927 (2004).), and (e) a coreceptor for Coxsackievirus A9 (Triantafilou et al., $J\ Virol.$ 76(2):633-643 (2002)). The results described here show for the first time that GRP78 acts as a receptor for fungal pathogens. GRP78 was found to act as a receptor for invasion but not adherence of Mucorales to endothelial cells. Similarly, N-cadherin was shown to mediate invasion but not adherence of $C.\ albicans$ to endothelial cells (Phan et al., $J$ Biol Chem. 280(11):10455-10461 (2005)), demonstrating that adherence and invasion are two independent processes mediated by different receptors. The fungal ligand for GRP78 that mediates invasion of endothelial cells is under active investigation.

With regard to the effect of iron on GRP78, previous work demonstrated paradoxical effects of iron on GRP78 expression in animal models. For example, mRNA and protein levels of GRP78 were decreased in iron-fed C57BL/6 mice, while they were unchanged in iron-fed 129/Sv mice (Faye et al., *Blood Cells Mol Dis.* 39(3):229-237 (2007)). In contrast, rats with chronic or acute iron overloaded had increased GRP78 expression in hearts and livers compared with control rats (Lou et al., *Clin Exp Pharmacol Physiol.* 36(7):612-618 (2009)). As described herein, iron was found to have a drastic effect on increasing the cell surface expression of GRP78. Higher glucose concentrations also increased expression of GRP78, but to a lesser extent. These results are in agreement with the findings of Mote et al., who reported that Chinese hamster lung fibroblasts expressed 30% more GRP78 when cultured in medium with a glucose concentration of 4.5 mg/ml compared with medium with a glucose concentration of 1.5 mg/ml (Mote et al., *Mech Ageing Dev.* 104(2):149-158 (1998)).

As described herein, the DKA mice have elevated available serum iron and increased serum glucose, and expressed more GRP78 in their organs. This underscore the physiological relevance of the above in vitro findings. Anti-GRP78 Ab was found to protected DKA mice from *R. oryzae* infection. The mechanism of immunological protection is currently under investigation.

In summary, through multiple independent lines of investigation, GRP78 was demonstrated to function as a receptor for Mucorales that facilitates fungus-induced penetration and subsequent damage of endothelial cells. Additionally, expression of the receptor and subsequent invasion of and damage to endothelial cells in a receptor-dependent manner were increased in the presence of elevated concentrations of iron and glucose, consistent with those seen in patients with DKA. Anti-GRP78 Ab was found to protected DKA mice from infection with mucormycosis. These results prove why DKA patients are uniquely susceptible to mucormycosis infections and provide methods and compositions for therapeutic interventions against extremely lethal mucormycosis.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method of treating mucormycosis comprising administering to a human subject having mucormycosis a composition, wherein the composition comprises a therapeutically effective amount of an isolated antibody or an antibody fragment thereof that specifically binds the human glucose-regulated protein, 78 kD polypeptide (GRP78) or an antigenic fragment thereof in said human subject, wherein said mucormycosis is caused by a *Rhizopus* species.

2. The method of claim 1, wherein said *Rhizopus* species is *Rhizopus oryzae*.

3. The method of claim 1, wherein the human subject is immunocompromised.

4. The method of claim 1, wherein the human subject is suffering from diabetes mellitus.

5. The method of claim 1, wherein the human subject is suffering from diabetic ketoacidosis.

6. The method of claim 1, wherein the human subject is suffering from trauma.

7. The method of claim 1, wherein the antibody or the antibody fragment thereof blocks the GRP78 and abrogates endocytosis of the *Rhizopus* species by endothelial cells expressing the GRP78 in said human subject.

8. The method of claim 1, wherein the antibody is a monoclonal antibody, or the antibody fragment is a fragment of said monoclonal antibody.

9. The method of claim 1, wherein the antibody is a humanized monoclonal antibody, or the antibody fragment is a fragment of said humanized monoclonal antibody.

* * * * *